(12) United States Patent
Kimura et al.

(10) Patent No.: US 6,814,742 B2
(45) Date of Patent: Nov. 9, 2004

(54) PHYSIOLOGICAL TISSUE CLIPPING APPARATUS, CLIPPING METHOD AND CLIP UNIT MOUNTING METHOD

(75) Inventors: Koh Kimura, Sagamihara (JP); Takayuki Suzuki, Yokohama (JP); Hiroyoshi Watanabe, Kunitachi (JP); Chika Shiro, Hachioji (JP)

(73) Assignee: Olympus Corporation, Tokyo (JP)

( * ) Notice: Subject to any disclaimer, the term of this patent is extended or adjusted under 35 U.S.C. 154(b) by 88 days.

(21) Appl. No.: 09/975,490

(22) Filed: Oct. 11, 2001

(65) Prior Publication Data
US 2002/0045909 A1 Apr. 18, 2002

(30) Foreign Application Priority Data

Oct. 16, 2000 (JP) .......................... 2000-315302
Aug. 10, 2001 (JP) .......................... 2001-244402

(51) Int. Cl.[7] .............................. A61B 17/08
(52) U.S. Cl. .................. 606/151; 606/157; 606/142
(58) Field of Search ................. 606/151, 157, 606/158, 142; 24/543, 546, 459; 206/368, 438

(56) References Cited

U.S. PATENT DOCUMENTS

| | | | | | |
|---|---|---|---|---|---|
| 3,958,576 | A | * | 5/1976 | Komiya | 606/142 |
| 4,367,746 | A | * | 1/1983 | Derechinsky | 606/142 |
| 4,733,664 | A | | 3/1988 | Kirsch et al. | |
| 5,156,609 | A | | 10/1992 | Nakao et al. | |
| 5,207,692 | A | * | 5/1993 | Kraus et al. | 606/143 |
| 5,242,456 | A | * | 9/1993 | Nash et al. | 606/142 |
| 5,392,917 | A | | 2/1995 | Alpern et al. | |
| 5,520,701 | A | * | 5/1996 | Lerch | 606/142 |
| 5,571,129 | A | | 11/1996 | Porter | |
| 5,766,189 | A | * | 6/1998 | Matsuno | 606/158 |
| 5,893,878 | A | | 4/1999 | Pierce | |
| 5,993,465 | A | * | 11/1999 | Shipp et al. | 606/142 |
| 6,402,765 | B1 | * | 6/2002 | Monassevitch et al. | 606/151 |

FOREIGN PATENT DOCUMENTS

| | | |
|---|---|---|
| DE | 27 35 706 B2 | 10/1979 |
| DE | 195 34 320 C1 | 2/1997 |
| DE | 195 34 323 A1 | 3/1997 |
| DE | 197 07 382 A1 | 9/1997 |
| DE | 298 06 611 U1 | 8/1998 |
| DE | 693 19 704 T2 | 3/1999 |
| DE | 197 40 847 C1 | 8/1999 |
| DE | 100 11 292 A1 | 9/2000 |
| EP | 0 529 297 B1 | 9/1995 |
| JP | 62-78901 | 5/1987 |
| JP | 2-239855 | 9/1990 |
| JP | 5-91686 | 12/1993 |
| JP | 8-19548 | 1/1996 |
| JP | 2713754 | 10/1997 |
| WO | WO 92/21400 | 12/1992 |
| WO | WO 93/09721 | 5/1993 |
| WO | WO 96/35460 | 11/1996 |
| WO | WO 97/43956 | 11/1997 |
| WO | WO 99/17830 | 4/1999 |
| WO | WO 99/19016 | 4/1999 |

* cited by examiner

Primary Examiner—David O. Reip
Assistant Examiner—Bradford C Pantuck
(74) Attorney, Agent, or Firm—Scully, Scott, Murphy & Presser

(57) ABSTRACT

A clipping apparatus comprises a clip capable of being arbitrarily opened/closed, a stop tube for closing the clip, a link member capable of being inserted into the stop tube, and engaged with the clip, a sheath section capable of housing the clip and the stop tube therein, and a manipulating wire inserted into the sheath section. This clipping apparatus further comprises a hook section for, when the clip and the stop tube is protruded frontally of the sheath section, causing the sheath section and the stop tube to be engaged with each other, and disabling the stop tube from being housed in the sheath section again.

33 Claims, 24 Drawing Sheets

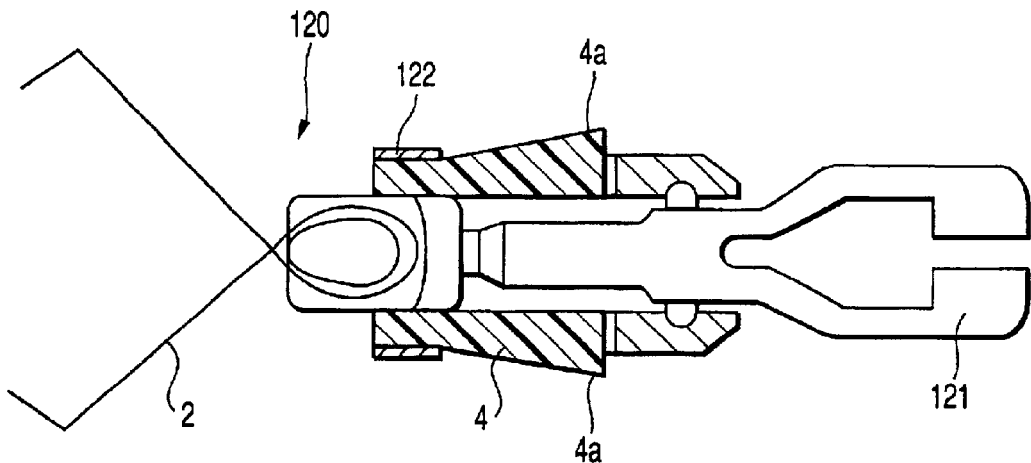
F I G. 29
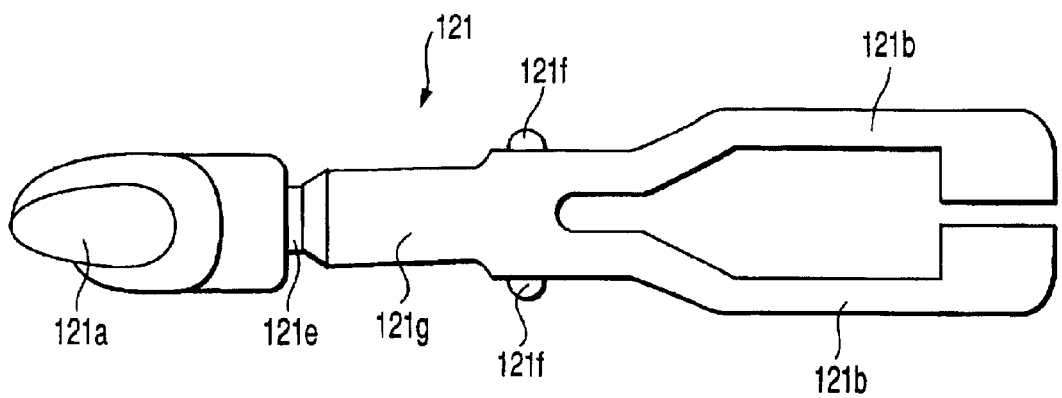
F I G. 30
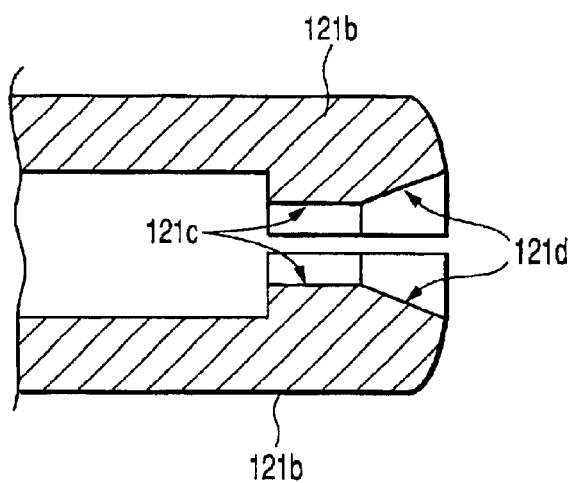
F I G. 31

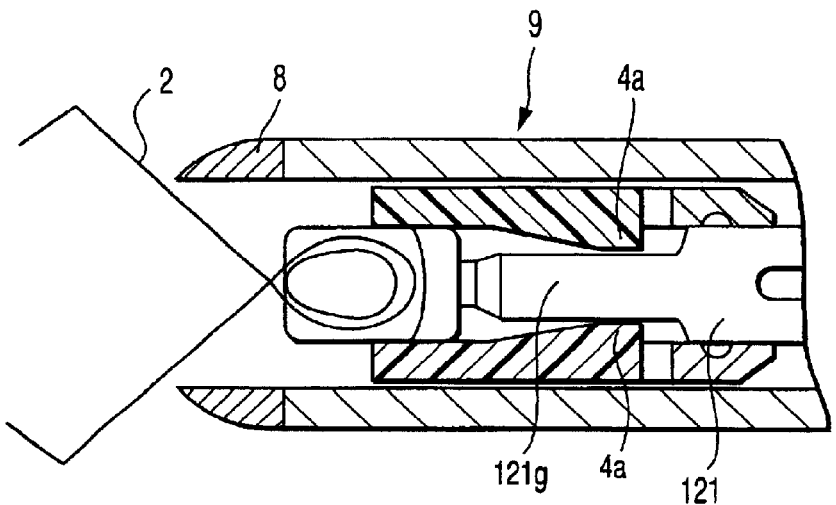
F I G. 32
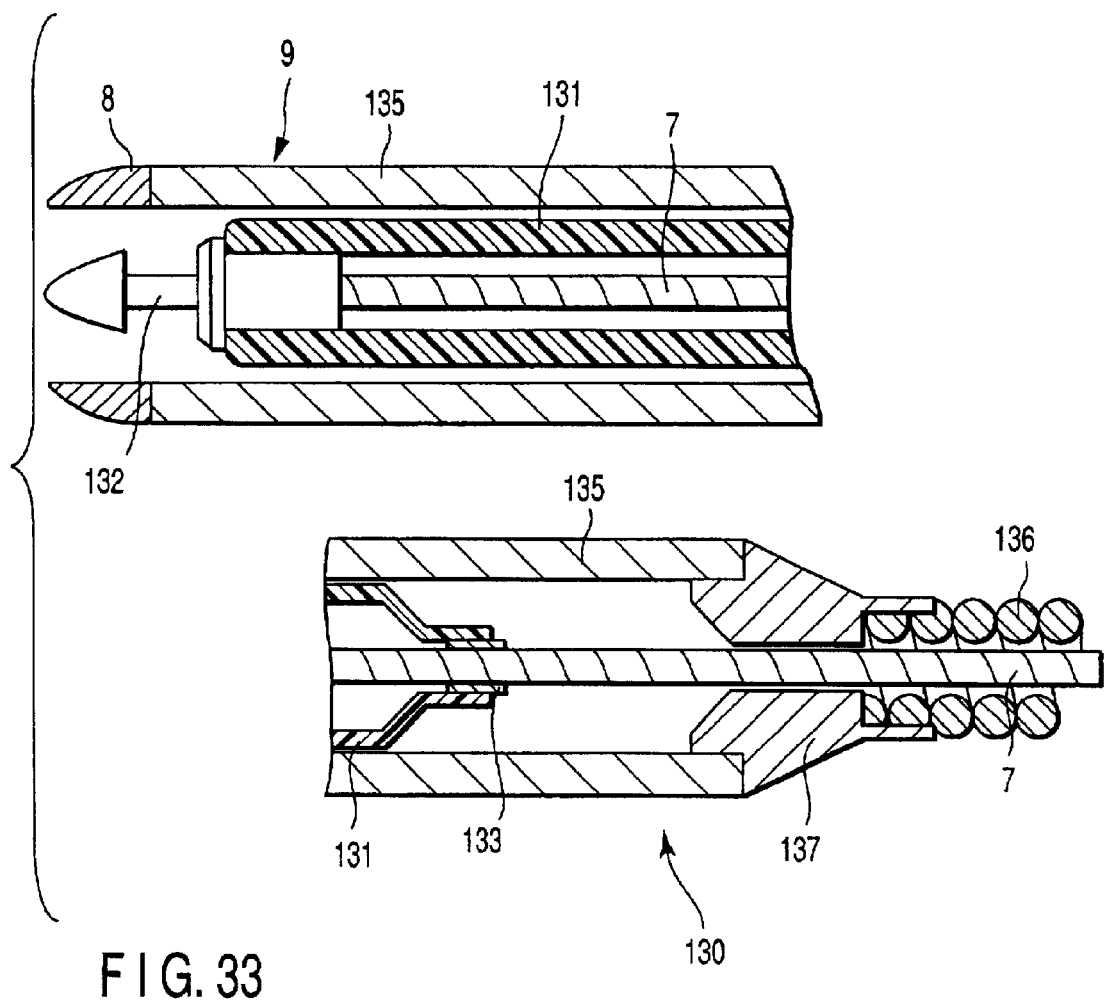
F I G. 33

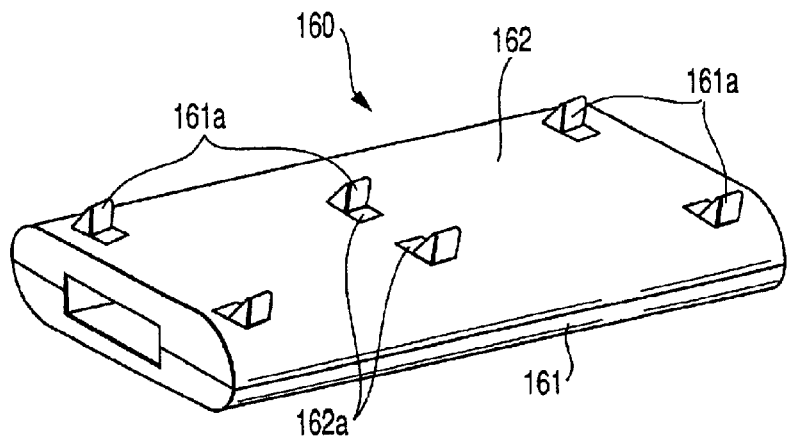
F I G. 40
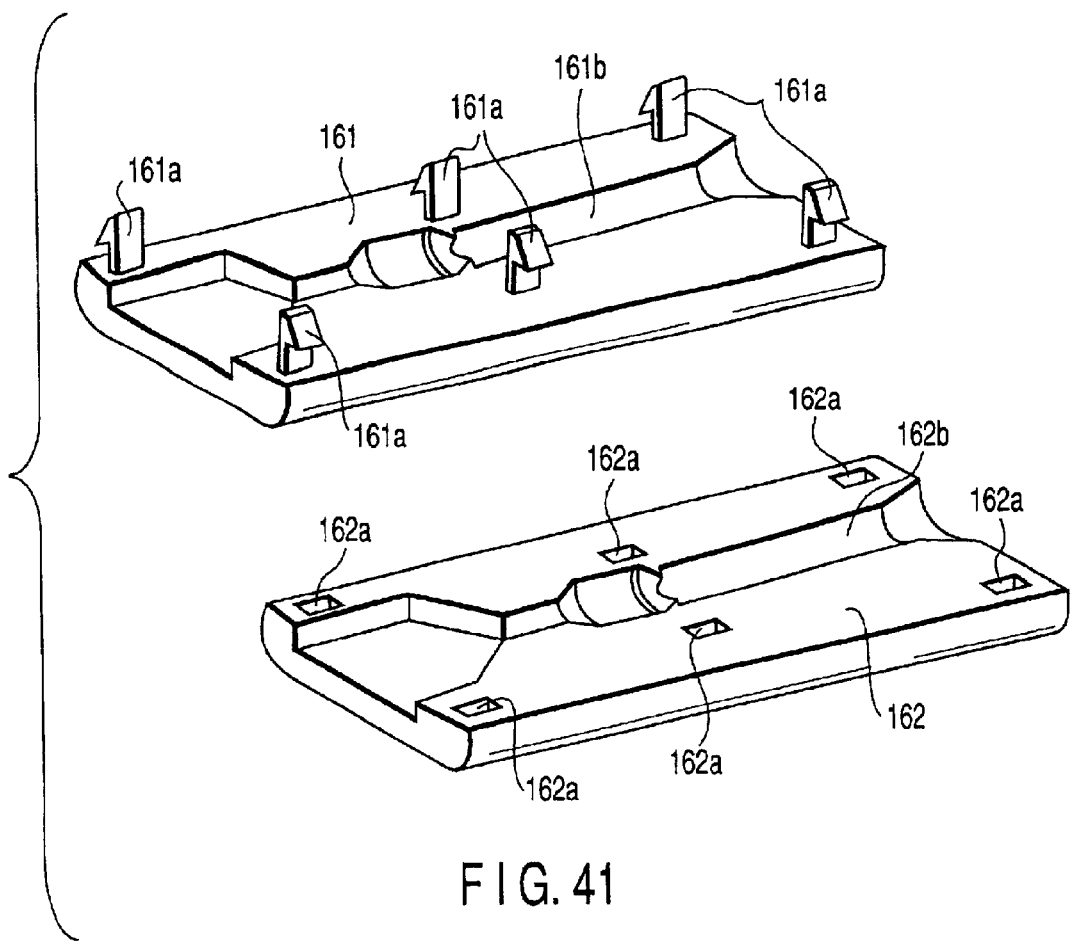
F I G. 41

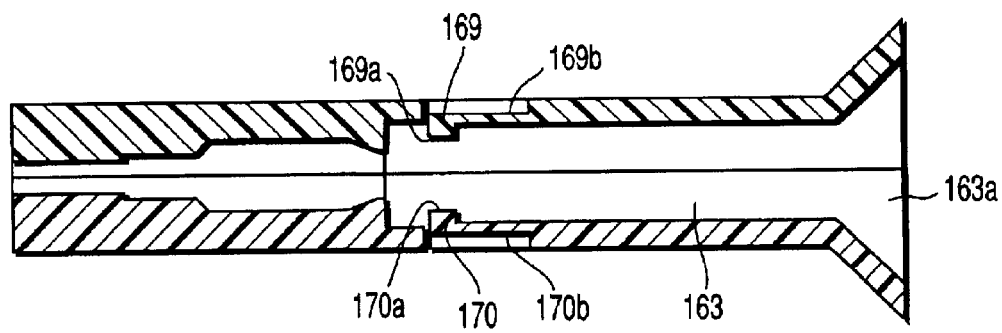
F I G. 42
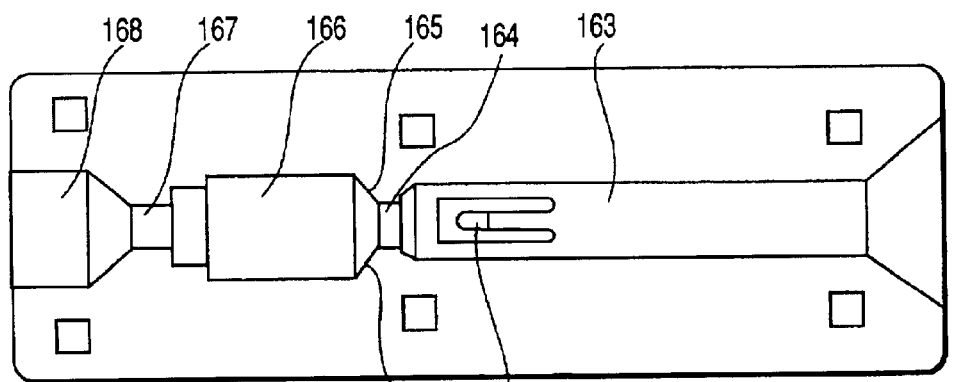
F I G. 43A
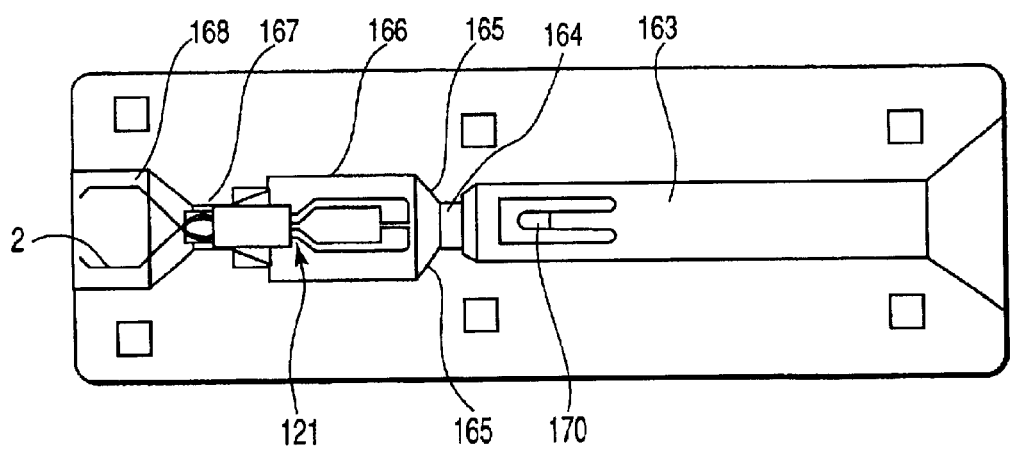
F I G. 43B

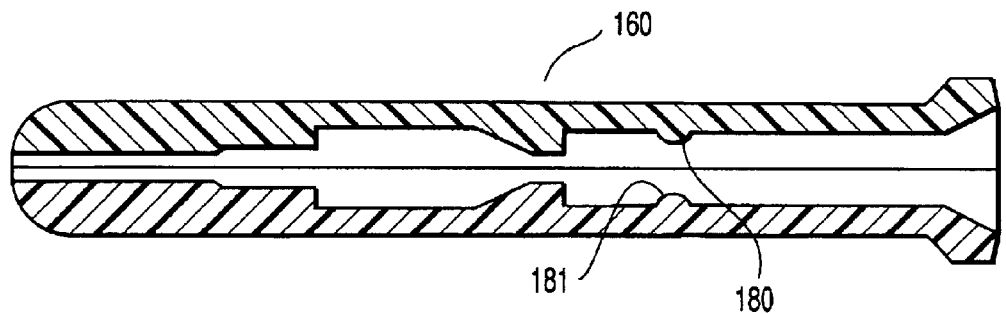
F I G. 44
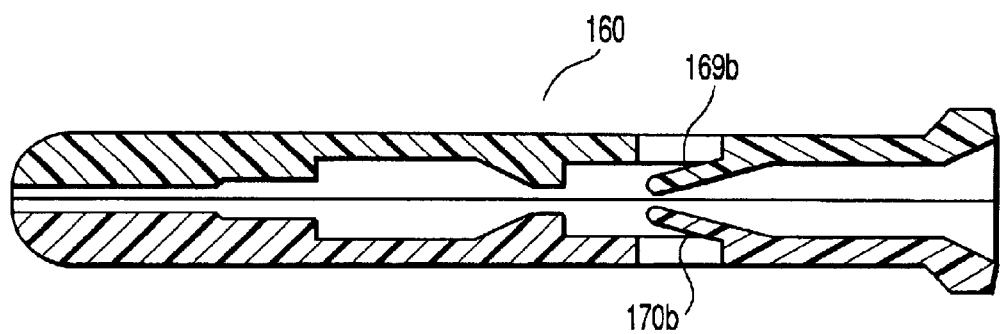
F I G. 45
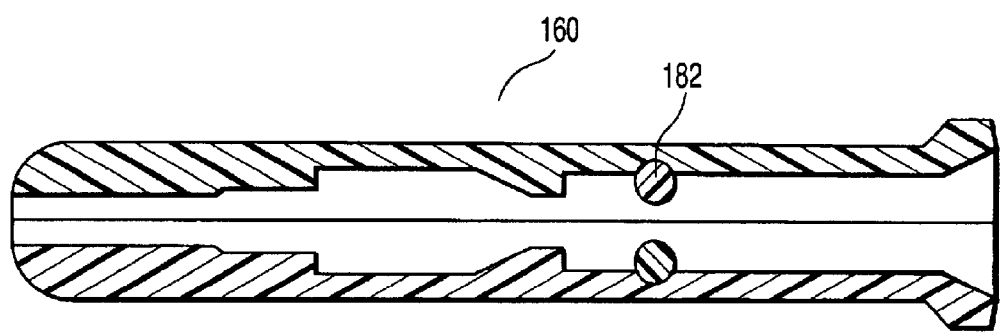
F I G. 46

PHYSIOLOGICAL TISSUE CLIPPING APPARATUS, CLIPPING METHOD AND CLIP UNIT MOUNTING METHOD

CROSS-REFERENCE TO RELATED APPLICATIONS

This application is based upon and claims the benefit of priority from the prior Japanese Patent Applications No. 2000-244402, filed Oct. 16, 2000; and No. 2001-244402, filed Aug. 10, 2001, the entire contents of both of which are incorporated herein by reference.

BACKGROUND OF THE INVENTION

1. Field of the Invention

The present invention relates to a physiological tissue clipping apparatus, clipping method and clip unit mounting method for inserting an endoscope into a cavity endoscopically, for example, and clipping a physiological tissue.

2. Description of the Related Art

As a physiological tissue clipping apparatus, there is known a mechanism disclosed in Japanese Patent Application KOKAI Publication No. 8-19548, for example. This clipping apparatus is composed of a clip unit 10 and a clip manipulating device 106, as shown in FIG. 28A and FIG. 28B. The clip unit 101 causes a link member 103 to be engaged with a clip 102, and further, engages a clip tightening ring 104. A link member 103 is composed of a plate material, and an engagement hole 103b is provided to be linked with a hook section 112 of the clip manipulating device 106.

The clip manipulating device 106 composed of an insert section 106a and a frontal manipulating section 106b. The insert section 106a is composed of an introducing tube 107, a manipulating tube 109 routed into the introducing tube 107, and a manipulating wire 110 routed into the manipulating tube 109. The hook section 112 having a pin 111 to be linked with a link member 103 is provided at the manipulating wire 110. The frontal manipulating section 106b is composed of: a tube joint 114 fixed frontally of the introducing tube 107; a manipulating section main body 115 for manipulating the manipulating tube 109 to be advanced or retracted; and a slider section 116 for manipulating the manipulating wire 110 to be advanced or retracted.

Therefore, the clip unit 101 is mounted on the clip manipulating device 106, and is introduced into a cavity in accordance with the following procedures.

(1) The manipulating section main body 115 is pushed against a tip end side, and the manipulating tube 109 is protruded from the introducing tube 107.
(2) The slider section 116 is pushed against a tip end side, and the hook section 103a is protruded from the manipulating tube 109.
(3) The pin 111 is engaged through the engagement hole 103b while the engagement hole 103b of the link member 103 of the clip unit 101 is aligned with the pin 111 of the hook section 112 of the clip manipulating device 106.
(4) The slider section 116 is pulled toward a proximal end side, and the tightening ring 104 of the clip unit 101 is engaged with a tip end of the manipulating tube 109.
(5) The manipulating section main body 115 is pulled to the proximal end side, and the clip unit 101 is stored in the introducing tube 107.
(6) The clip unit is introduced into a cavity via an endoscope.

Next, the clip unit 101 is ligated in accordance with the following procedures.

(1) The manipulating section main body 115 is pushed to the tip end side, and the clip unit 101 is protruded from the inside of the introducing tube 107.
(2) The slider section 116 is slightly pulled toward the proximal end side, and the clip 102 is placed in an expanded state.
(3) The slider section 116 is pulled toward the proximal end side, the tightening ring 104 is engaged with the clip 102, and the clip 102 is ligated.

In addition, as a configuration of the introducing tube and the manipulating wire, for example, an endoscope treatment tool disclosed in Japanese Patent Application KOKAI Publication No. 2-239855 is known. Structurally, this endoscope treatment tool comprises: an external sheath tube; a manipulating wire retractably inserted into this external sheath tube to be advanced and retracted by manipulation from the frontal side; a treatment section mounted on this manipulating wire, the treatment section being capable of manipulating the treatment tool at the tip end side of the external sheath tube by advancement and retraction of such manipulating wire and being configured by an elastic wire; an extension section wire expanding at least one end of this elastic wire, the extension section wire being introduced into the external sheath tube; and a plurality of bent sections forming either of this extension section wire and the above manipulating wire to be bent in the external sheath tube and securely mounting it to another one.

Therefore, when this endoscope treatment tool advances and retracts a manipulating wire by manipulating a manipulating section, and actuates a treatment section, slackness is reduced in the external sheath tube of the manipulating wire or extension section wire. Therefore, a loss of a manipulating quantity of the manipulating section is very small, and the treatment section at the tip end of the external sheath tube can be reliably manipulated.

In addition, as a configuration of the introducing tube and the manipulating wire, an endoscope injector disclosed in Japanese Utility Model Application KOKAI Publication No. 5-91686 is known. This endoscope injector is such that a manipulating section and a puncture section are linked with each other via a double tube composed of an internal sheath tube and an external sheath tube. A protrusion quantity restricting member for stabilizing a projection quantity of an injection needle provided at a tip end of the internal sheath tube is provided at a tip end of the external sheath tube, and a side face of a stopper and a side face of a protrusion quantity restricting member are slid each other, whereby the movement quantity of the injector needle is restricted.

Further, a configuration of the manipulating section, an endoscope injector disclosed in Japanese Utility Model Application KOKAI Publication No. 62-78901 is known. This injector comprises: an injection tube having flexibility; a tubular tip end needle mounted on a tip end of this injection tube; a flexible external sheath tube having the tip end needle and the injection tube slidably routed; an injection pipe connected to a proximal end of the injection tube at the frontal inside of this external sheath tube; and a fixing mechanism for, when the tip end needle provided at the tip end part of the external sheath tube protrudes from the tip end of the external sheath tube, and is restricted in abutment against the stopper, compressing this injection tube to be fixed to the external sheath tube.

However, in the clipping apparatus disclosed in Japanese Patent Application KOKAI Publication No. 8-19548, a tube joint 114 for advancing and retracting an introducing tube 107, a manipulating section main body 115 for advancing and retracting a manipulating tube 109, and a slider section 116 for advancing and retracting the manipulating wire 110 are provided at frontally of a manipulating section 106b.

Therefore, over six steps between (1) and (2), it is required to manipulate the tube joint 114, manipulating section main body 115, and manipulating wire 110 to be advanced and retracted, which complicates manipulation.

In addition, the following steps are required to mount the clip unit 101 on the hook section 112:

(1) the link member 103 of the clip unit 101 is held in a horizontal direction relevant to a cutout provided at the hook section 112;
(2) the pin 111 provided at the hook section 112 is engaged with the engagement hole 113b provided at the link section 113 while they are aligned with each other so that the pin 111 is engaged with the engagement hole 103b. Thus, two steps of (1) orientation and (2) alignment must be carried out at the same time, making it difficult to carry out a mounting work.

In order to ligate the clip unit 101, the clip 102 is held to the maximally opened state, making it necessary to ligate a target site in this state. However, if manipulation is incorrect, the maximally opened state is passed, making it impossible to ligate the target site. Thus, the slider section 116 must be carefully manipulated, which makes manipulation difficult.

In the Japanese patent Application KOKAI Publication No. 2-239855, the slackness of a wire when the manipulating wire can be eliminated in consideration of application of the clip manipulating device to the manipulating wire.

However, when the introducing tube is bent, the manipulating wire slips out of an axial center of the introducing tube. Therefore, when the clip unit is mounted on the hook section, the position of the hook section is changed according to the shape of the introducing tube, and can be safely fixed, thus making it difficult to mount the clip unit on the hook section.

In addition, in Japanese Patent Utility Model Application KOKAI Publication No. 5-91686, the hook section can be positioned at the axial center of the introducing tube in consideration of application of the clip manipulating device to the hook section and introducing tube. However, a structure is mandatory such that a tip end part of the introducing tube is contracted in a tapered shape. When the contraction section is defined as an internal diameter through which the clip unit can pass, an external diameter of the introducing tube is increased. In addition, in order to enable the hook section to be reliably engaged with the link member of the clip unit, the length of the hook section must be fully protruded from the tip end of the introducing tube. Because of this, the length of the hook section is increased, the flexibility of the introducing tube is lost when the hook section is pulled into the introducing tube, making it difficult to ensure routing into a soft endoscope or protrusion of the hook section.

Further, in consideration of the fact that a fixing mechanism of a manipulating section disclosed in Japanese Utility Model Application KOKAI Publication No. 62-78901 is applied to a fixing mechanism of a slider of a clip manipulating device, in a fixing mechanism caused by an elastic rubber ring, an amount of the actuation force when the slider is fixed is equal to that when the slider is released. In order to facilitate fixing, when an elastic rubber ring with a small amount of force is employed, the release can be ensured with a small amount of force similarly, making it impossible to ensure reliably fixing. Conversely, when an elastic rubber ring with a large amount of force is employed in order to make the release difficult, the fixing becomes heavy, makes it difficult to make manipulation.

BRIEF SUMMARY OF THE INVENTION

The present invention has been made in order to solve the foregoing problem. It is an object of the present invention to provide a physiological tissue clipping apparatus capable of inserting a clip into a physiological cavity while the clip is housed in an introducing tube, and further engaging the housed clip at the same time when the clip is released from the introducing tube merely by manipulating a manipulating member to be advanced and retracted, capable of ligating the clip, and capable of being easily handled.

According to one aspect of the present invention, there is provided a clipping apparatus comprising:

a clip capable of being arbitrarily opened/closed;

a tightening ring engagingly mounted on this clip, thereby closing the clip;

a link member capable of being inserted into this tightening ring and engaged with the clip;

an introducing tube capable of housing the clip and the tightening ring;

a manipulating member retractably routed into this introducing tube; and engagement means provided at at least one of the tightening ring and the introducing tube, the engagement means engaging the introducing tube with the tightening ring when the clip and tightening ring protrudes in front of the introducing tube, and disabling the tightening ring from being housed again in the introducing tube.

According to another aspect of the present invention, there is provided a clipping apparatus comprising:

a clip capable of being arbitrarily opened/closed;

a tightening ring engagingly mounted on this clip, thereby closing the clip;

a link member capable of being inserted into this tightening ring and engaged with the clip;

an introducing tube capable of housing the clip and the tightening ring;

a manipulating member retractably routed into this introducing tube; and a cover provided on the clip capable of entering an opened state required to ligate a physiological tissue from a closed state capable of being inserted into an endoscope.

According to another aspect of the present invention, there is provided a clipping apparatus comprising:

a clip capable of being arbitrarily opened/closed;

a tightening ring engagingly mounted on this clip, thereby closing the clip;

a link member capable of being inserted into this tightening ring and engaged with the clip; and a manipulating wire having a hook at its tip end, wherein, when the link member is set at an arbitrary peripheral position relevant to an axial direction of the hook, at least one of the link member and the hook is deformed and restored, whereby the link member and the hook are engaged with each other.

According to another aspect of the present invention, there is provided a clipping apparatus comprising:

a clip capable of being arbitrarily opened/closed;

a tightening ring engagingly mounted on this clip, thereby closing the clip;

a link member capable of being inserted into this tightening ring and engaged with the clip; and holding means for, when the clip is opened to the maximum, temporarily holding the opened state.

According to another aspect of the present invention, there is provided a clipping apparatus comprising:

a clip capable of being arbitrarily opened/closed, the clip being made of an ultra-elastic alloy;

a tightening ring engagingly mounted on this clip, thereby closing the clip; and a link member capable of being inserted into this tightening ring and engaged with the clip.

According to the physiological tissue clipping apparatus, the link member is engaged with the clip, and further, the tightening ring is mounted on the manipulating wire as a manipulating member. Then, the manipulating member is manipulated, all of the clip, link member, and tightening ring are housed in the introducing tube to be introduced into a cavity. After this introduction, the manipulating member is manipulated, the clip, link member, and tightening ring are protruded to the outside of the introducing tube, and the introducing tube and the tightening ring are engaged with each other. Then, the manipulating member is manipulated again, the tightening ring is engaged with the tightening ring, and the clip is ligated. Therefore, merely by manipulating the manipulating member to be advanced and retracted, the housed clip can be engaged at the same time when the clip is released from the introducing tube, and the clip can be ligated.

According to another aspect of the present invention, there is provided a physiological tissue clipping method comprising:

a first step of connecting a clip unit housed in a clip case on a clip manipulating device;

a second step of routing the clip manipulating device into a soft endoscope, thereby guiding the clip unit into a target site of a physiological tissue; and a third step of manipulating the clip manipulating unit, thereby clipping the clip unit at the physiological tissue.

According to the present invention, there is provided a physiological clipping method comprising:

a first step of connecting a clip unit housed in a clip case with a clip manipulating device, and manipulating the clip manipulating device, thereby mounting the clip unit on the clip manipulating device;

a second step of routing the clip manipulating device into a soft endoscope, thereby guiding the clip unit into a target site of a physiological tissue; and a third step of manipulating the clip manipulating unit, thereby clipping the clip unit at the physiological tissue.

According to the physiological tissue clipping method, a series of operations can be easily made such that the clip unit in the clip case is mounted on the clip manipulating device, this clip manipulating device is pulled toward the target site of the physiological tissue, and the clip unit is clipped at the physiological tissue.

According to another aspect of the present invention, there is provided a clip unit mounting method comprising:

a first step of connecting a clip manipulating member in a clip case to a clip unit; and a second step of mounting the clip unit housed in the clip case on a clip manipulating device.

According to another aspect of the present invention, there is provided a clip unit mounting method comprising:

a first step of connecting a clip unit housed in a clip case with a sheath of a clip manipulating device having a clip manipulating member retractably inserted thereinto;

a second step of advancing the clip manipulating member, thereby connecting the clip unit with the clip manipulating member in the clip case; and a third step of retracting the clip manipulating member, thereby guiding the clip unit housed in the clip case to the inside of the sheath, and mounting the guided clip unit thereon.

According to the clip unit mounting method, a series of operations can be easily made such that the clip unit housed in the clip case is pulled in by the clip manipulating device, and the guided clip unit is mounted on the clip manipulating device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a longitudinally sectional side view of a clip unit, FIG. 1B is a side view of a clip, FIG. 1C is a perspective view of a link member; FIG. 1D is a perspective view of a stop tube, and FIG. 1E is a longitudinal side view of the stop tube having the clip mounted thereto;

FIG. 2A is a side view of a clip manipulating device, FIG. 2B is a perspective view of a hook section, and FIG. 2C is a longitudinal side view of the hook section;

FIG. 11A is a longitudinal side view of a clip unit, FIG. 11B is a perspective view of the same, and FIG. 11C is a side view of a first link member;

FIG. 13A and FIG. 13B each show a fifth embodiment of the present invention, wherein FIG. 13A is a longitudinal side view of a clip unit, and FIG. 13B is a perspective view of a link member;

FIG. 15A is a longitudinal side view of a clip unit, FIG. 15B is a perspective view of the same, and FIG. 15C is an exploded perspective view of the same;

FIG. 18A is a longitudinally sectional side view of a clip unit and a clip cover, FIG. 18B is a side view of a link member, and FIG. 18C is a side view of the clip cover:

FIG. 19A to FIG. 19D each show a ninth embodiment according to the present invention, wherein FIG. 19A is a side view of a clip unit and a clip cover, and FIG. 19B, FIG. 19C, and FIG. 19D are perspective views each illustrating an operation according to the illustrative embodiment;

FIG. 20A is a side view of a clip unit and a clip cover, and FIG. 20B and FIG. 20C are side views each illustrating an operation according to the illustrative embodiment;

FIG. 22A is a perspective view of a clip unit, FIG. 22B is a perspective view of a clip, and FIG. 22C is a partially enlarged side view of the clip;

FIG. 23A is a perspective view of a clip unit, and FIG. 23B is a perspective view of a clip;

FIG. 28A is a longitudinally sectional side view of a clip unit and a clip manipulating device, and FIG. 28B is a longitudinally sectional side view of the clip manipulating device;

FIG. 29 shows an eighteenth embodiment according to the present embodiment, and is a longitudinally sectional side view of a clip unit;

FIG. 30 is a side view showing a link member according to the illustrative embodiment;

FIG. 31 is a longitudinally sectional side view showing a part of a link member according to the illustrative embodiment;

FIG. 32 is a longitudinally sectional side view showing a tip end of a coil sheath according to the illustrative embodiment;

FIG. 33 is a longitudinally sectional side view showing a coil sheath according to the illustrative embodiment;

FIG. 40 shows a twenty first embodiment according to the present invention, and is a perspective view of a clip case;

FIG. 41 is a perspective view when a case main body of a clip case and a case cover according to the present embodiment are separated from each other;

FIG. 42 is a longitudinally sectional side view showing the clip case according to the illustrative embodiment;

FIG. 43A and FIG. 43B are plan views each showing the case cover according to the illustrative embodiment;

FIG. 44 shows a twenty second embodiment according to the present invention, and is a longitudinally sectional side view of a clip case;

FIG. 45 shows a twenty third embodiment according to the present invention, and is a longitudinally sectional side view of a clip case;

FIG. 46 shows a twenty fourth embodiment according to the present invention, and is a longitudinally sectional side view of a clip case;

DETAILED DESCRIPTION OF THE INVENTION

Hereinafter, preferred embodiments of the present invention will be described with reference to the accompanying drawings.

Figure 1A:
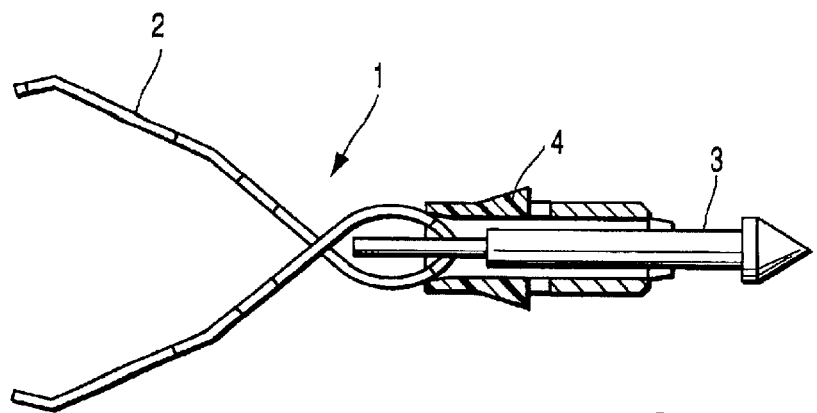
FIG. 1A to FIG. 1E each show a first embodiment according to the present invention, where
Figure 1B:
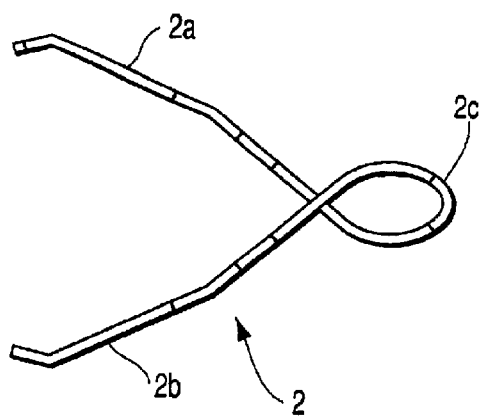
Figure 1C:
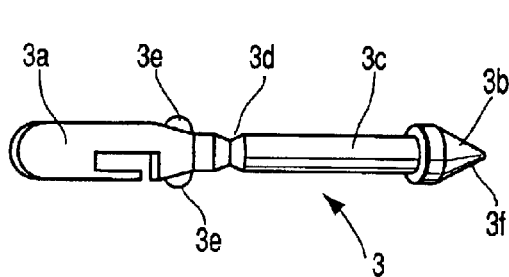
Figure 1D:
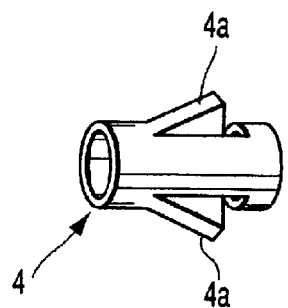
Figure 1E:
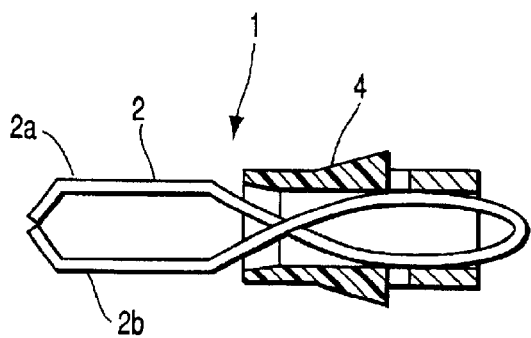
Figure 2A:
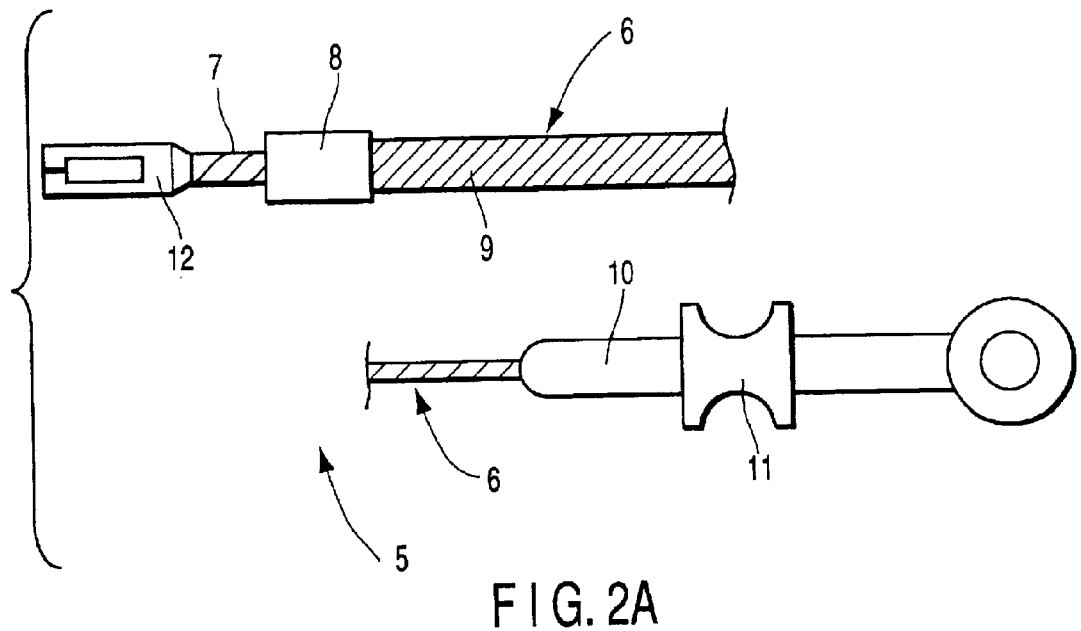
FIG. 2A to FIG. 2C each show the illustrative embodiment according to the present invention, where

FIGS. 1A–1E to FIG. 6 each show a first embodiment, where a physiological tissue clipping apparatus is composed of a clip unit 1 shown in FIG. 1A and a clip manipulating device 5 shown in FIG. 2A. The clip unit 1 has a clip 2, a link member 3 as a link member, and a stop tube 4 as a clip tightening ring.

The clip 2 comprises a metal plate, such as a plate spring member, bent at its center, and further, crosses a position in the vicinity of a bent section as shown in FIG. 1B. Then, arm sections 2a and 2b being openable, the arm sections being capable of being arbitrarily opened/closed, are provided, respectively, to be extended while their tip ends are spaced from each other. A substantially elliptical proximal end 2c is formed at a proximal end side.

The link member 3 is fabricated by ejection-molding a resin such as a liquid crystal polymer or a nylon, for example. At a tip end of this link member 3, a claw shaped claw hook 3a is formed as shown in FIG. 1C. This claw hook 3a hooks an end part 2c at the proximal end side of the clip 2 so as to engage the clip 2.

Further, at the other end of the link member 3, an arrowhead hook 3b is formed to be linked with the clip manipulating device 5. A cone shape having an inclined face 3f is formed at the proximal end side of the arrowhead hook 3b. A maximum outer diameter of the arrowhead hook 3b ranges from 1.0 mm to 1.4 mm in diameter in consideration of a deformation quantity of elastic arms 12a and 12b of the hook section 12 described later.

In addition, it is desirable that the inclined face 3f is set to 30 degrees or less in order to smoothly mount the face on the hook section 12. A cylindrical cylinder section 3c having a smaller diameter than that of the tip end of the arrowhead hook 3a is provided between a claw hook 3a and the arrowhead hook 3b. Therefore, a step is formed at the boundary between the cylinder section 3c and the arrowhead hook 3b to be reliably engaged with the hook section 12. The outer diameter of the cylinder section 3c ranges from 0.7 mm to 1.0 mm in diameter in consideration of a step height influenced by an amount of engagement force with the hook section 12 and the tensile stress of the cylinder section 3c itself.

Further, a fracture section 3d having a diameter of 0.4 mm to 0.6 mm in diameter is provided at a distal end side of the cylinder section 3c. When an amount of tensile force of about 3 kgf to 5 kgf is applied to the link member 3, the link member breaks at the fracture section 3d. In addition, an arc shaped protrusion 3e having a slightly larger diameter than an inner diameter of a stop tube 4 described later, the protrusion coming into pressure contact with an internal face of the stop tube 4 for the purpose of fixing the link member 3 and stop tube 4 at a predetermined position, are provided at the proximal end side of the claw hook 3a. The link member 3 may be fabricated by ejection-molding a metal in order to ensure higher fracture strength.

The stop tube 4 is fabricated by ejection-molding a resin having high rigidity such as PBT (polybutytelephthalate) and having proper flexibility. The stop tube 4 is engagingly mounted on the arm sections 2a and 2b of the clip 2 as shown in FIG. 1E, thereby closing the arm sections 2a and 2b of the clip 2, and is substantially tubular in 1.2 mm to 1.3 mm in inner diameter and in 1.9 mm to 2.1 mm in outer diameter.

In a standby state before making an operation for closing the clip 2, as shown in FIG. 1A, these arm sections are held while each of them is externally engaged at a tip end part of the link member 3. In addition, a pair of protrusions 4a elastically deformed, the protrusions being placed to be arbitrarily protruded and recessed in the outer periphery direction of the stop tube 4 for the purpose of engagement with a coil pipe 8 described later (refer to FIG. 2A), are provided at the stop tube 4. The outer diameter when the protrusion 4a is protruded is set to 2.2 mm or more in consideration of engagement with the coil pipe 8.

In addition, the protrusion 4a is formed in an R shape between an inclined face having an angle of 30 degrees or less at a tip end side or a face vertical to the proximal end side, and a face vertical to this inclined face. This protrusion is extruded with a small amount of force when it is protruded at a tip end from the inside of a sheath section 6 described later, and is reliably engaged with the coil pipe 8 after protrusion. In addition, an inclined face is formed at the tip end side, thereby making it possible to effectively receive the force applied to a vertical face of the protrusion 4a during engagement with the coil pipe 8. The protrusion 4a may be provided in plurality (three or four and more) in order to stabilize engagement with the coil pipe 8 described later (refer to FIG. 2A) more remarkably.

Now, a configuration of a clip manipulating device 5 shown in FIG. 2A to FIG. 2C will be described here. As shown in FIG. 2A, a sheath section 6 having flexibility and a manipulating wire 7 as a manipulating member retractably inserted into this sheath section 6, are provided at the clip manipulating device 5.

A coil pipe 8 having an outer diameter that is greater than that of a stop tube 4 and smaller than that when a protrusion 4a is protruded and a coil sheath 9 having an inner diameter greater than the outer diameter of the stop tube 4 described previously, are provided at the sheath section 6. In addition, a manipulating section main body 10 is linked with a frontal side of the coil sheath 9. A slider 11 is connected with a frontal extension end of the manipulating wire 7. The slider 11 is retractably placed in the manipulating section main body 10 so that the manipulating wire 7 can be manipulated to be advanced/retracted relevant to the sheath section 6.

In addition, a hook section 12 is connected at a tip end of the manipulating wire 7. The hook section 12 is made of a resilient metal material. As shown in FIG. 2B and FIG. 2C, two elastic arms 12a and 12b having closing properties and a cylinder section 3c of the link member 3 are pinched, whereby pinch sections 12c and 12d engaged with the arrowhead hook 3b are provided. The elastic arms 12a and 12b are 0.2 mm to 0.4 mm in thickness and 0.5 mm to 1 mm in width. Its outer surface is formed in a arc shape of 1.8 mm to 2 mm in diameter, and the length ranges from 4 mm to 8 mm.

In addition, a semi-circular groove 12f having a diameter equal to an outer diameter of the cylinder section 3c is provided at the inside of the pinch sections 12c and 12d so as to easily held in pressure contact with the cylinder section 3c of the link member 3 by the closing force of the elastic arms 12a and 12b.

Figure 2B:
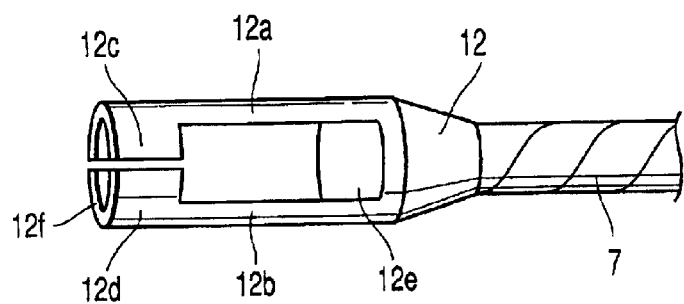
Figure 2C:
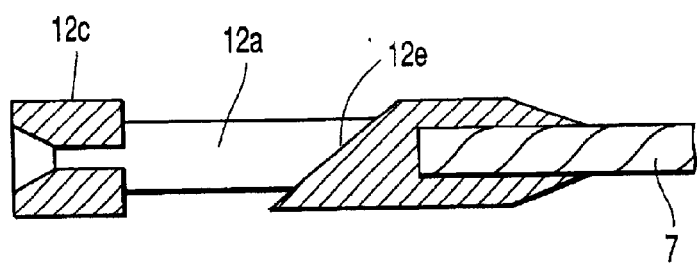

In addition, an inclined face 12e is provided at the proximal end part of the elastic arms 12a and 12b of the hook section 12 as shown in FIG. 2B and FIG. 2C. It is desirable that an angle of the inclined face 12e be set to 30 degrees or less in order to smoothly remove the link member 3 from the hook section 12. In addition, it is desirable that the elastic arms 12a and 12b and the pinch sections 12c and 12d of the hook section 12 is composed of an integral spring member in order to ensure higher strength. Further, the hook section 12 may be fabricated by molding a resin having high rigidity such as nylon, for example, and having resilient properties.

Figure 3A:
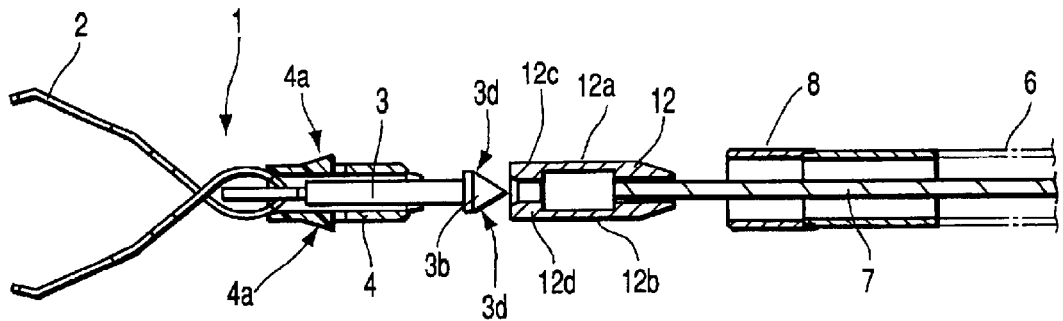
FIG. 3A to FIG. 3C each illustrate an operation of the illustrative embodiment according to the present invention, where the clip unit is connected to the clip manipulating device.

Now, an operation of the first embodiment will be described here. In order to mount the clip unit 1 on the clip manipulating device 5, first, as shown in FIG. 3A, the slider 11 is manipulated to be pushed against a tip end side. In this manner, the arrowhead hook 3b of the link member 3 is pushed at the tip end side against the tip end side of the hook section 12 while the hook section 12 is protruded from the coil pipe 8. Then, an internal face at the tip end side of the pinch sections 12c and 12d of the hook section 12 abuts against the inclined face 3f on the arrowhead hook 3b of the link member 3, and the pinch sections 12c and 12d are pushed to be broadened to the outside along the inclined face 3f.

At this time, the elastic arms 12a and 12b are elastically deformed. When the link member 3 is further pushed against the hook section 12, the pinch sections 12c and 12d are closed by the closing force of the elastic arms 12a and 12b when they pass through the arrowhead hook 3b, and the cylinder section 3c is pinched between the pinch sections 12c and 12d. At this time, the tip end face of the arrow hook 3b of the link member 3 abuts against the proximal end face of the pinch sections 12c and 12d. Thus, the arrowhead hook 3c cannot be removed from the hook section 12c, and the clip unit 1 is fixed to be hooked by the hook section 12.

Figure 3B:
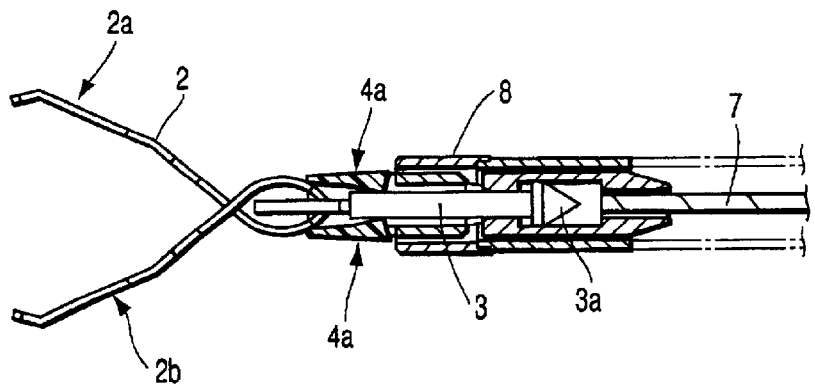

Then, as shown in FIG. 3B, while the protrusion 4a of the stop tube 4 is fully pushed into the stop tube 4, when the slider 11 is pulled into the proximal end side, the manipulating wire 7 and the hook section 12 are pulled into the coil sheath 9. At this time, the protrusion 4a of the step tube 4 is pushed into the stop tube 4, and thus, the clip unit 1 is pulled into the coil sheath 9 without being caught by an end face of the coil pipe 8.

At this time, the arm sections 2a and 2b of the clip 2 of the clip unit 1 is closed in accordance with the inner diameter of the coil sheath 9, and the coil unit 1 is housed in the coil sheath 9 as shown in FIG. 3. At this time, the protrusion 4a of the stop tube 4 comes into contact with the internal face of the coil sheath 9, and thus, is elastically deformed, thereby maintaining a state in which the protrusion is housed in the stop tube 4. In this state, the sheath section 6 is introduced into a cavity via a forceps channel of an endoscope inserted into the cavity in advance, and a tip end of the sheath section 6 is pulled toward a target site while the inside of the cavity is observed by the endoscope.

Figure 4A:
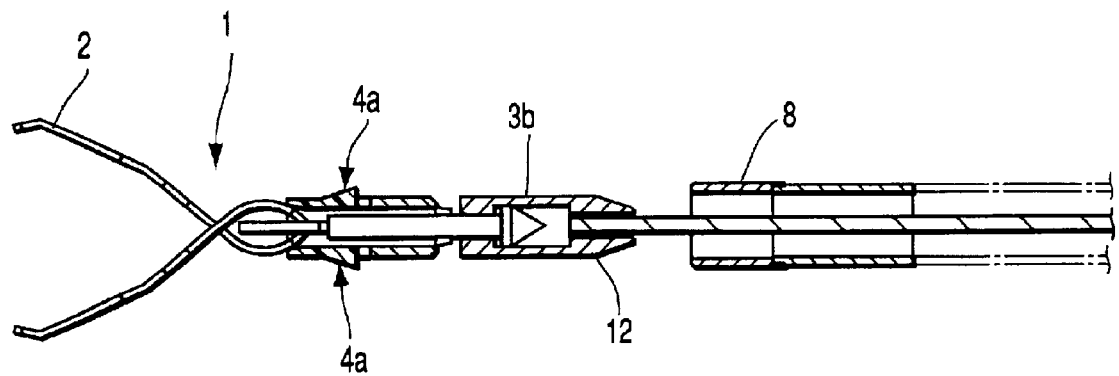
FIG. 4A to FIG. 4C each illustrate an operation of the illustrative embodiment according to the present invention, where the clip unit is connected to the clip manipulating device.

Next, the slider 11 is manipulated to be pushed out against the tip end side again, whereby the clip unit 1 is extruded from the coil pipe 8 as shown in FIG. 4. At this time, an inclined face is formed at the tip end side of the protrusion 4a of the stop tube 4 so that the clip unit 1 is pushed out smoothly and without any resistance. Then, the protrusion 4a of the stop tube 4 is released from a state of contact with the internal face of the coil sheath 9, and is protruded from the stop tube 4 in the outer periphery direction. At this time, the clip unit 1 is fixed to be pinched between the pinch sections 12a and 12d of the hook section 12 so as not to slip out of the hook section 12.

Figure 4B:
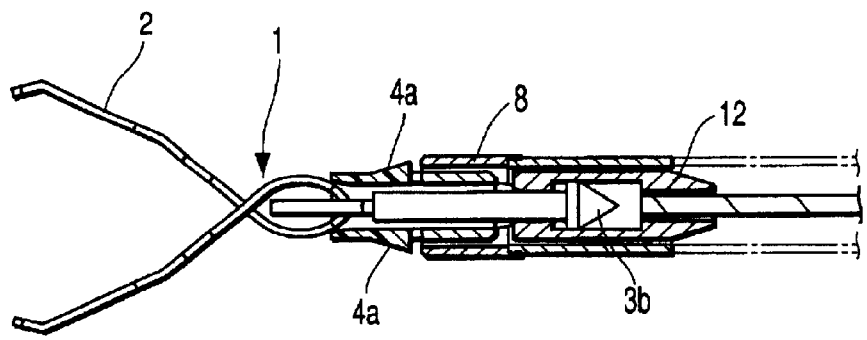
Figure 4C:
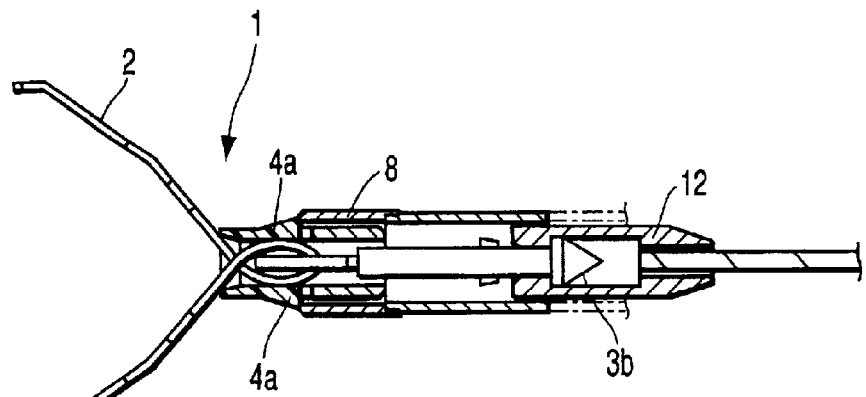

Then, the slider 11 is pulled toward the proximal end side again, whereby the manipulating wire 7 is pulled toward the proximal end side as shown in FIG. 4B, and the proximal end face of the protrusion 4a of the stop tube 4 is engaged with an end face of the coil pipe 8. When the slider 11 is further pulled toward the proximal end, an elliptic section dimension W of the end part 2c at the proximal end side of the clip 2 is greater than the inner diameter dimension of the stop tube 4 so that the elliptic section of the end part 2c at the proximal end side of the clip 2 is clashed by being pulled toward the stop tube 4. Then, the arm sections 2a and 2b open significantly in the outward direction as shown in FIG. 4C.

Figure 5:
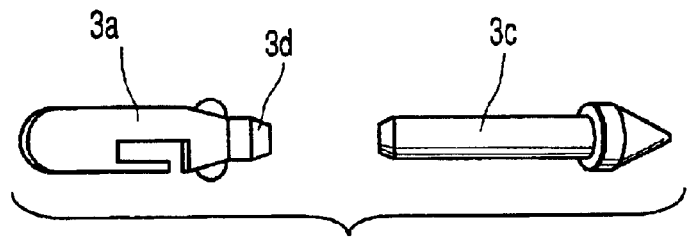
FIG. 5 is a view illustrating an operation of the sane embodiment according to the present invention and a perspective view of the link member.

In this state, the clip 2 is guided so as to pinch a target physiological tissue. Then, when the slider 11 is further pulled toward the proximal end side, thereby retracting the manipulating wire 7, the arm sections 2a and 2b of the clip 2 are pulled into the stop tube 4, and the arm sections 2a and 2b of the clip 2 are closed as shown in FIG. 1E. While the physiological tissue is reliably pinched between the arm sections 2a and 2b of the clip 2, when the slider 11 is further pulled toward the proximal end, thereby retracting the manipulating wire 7, the fracture section 3d of the link member 3 of the clip 2 breaks, as shown in FIG. 5. Then, the clip 2 is disengaged from the link member 3, and the clip unit 1 is released from the clip manipulating device 5, and then, is left in a cavity while the physiological tissue is pinched.

For example, the tissue at the bleeding site in the cavity is compressed by being pinched between the arm sections 2a and 2b of the clip 2, and the clip unit 1 is left while in that state, thereby making it possible to compress the blood vessel at the bleeding site and stop bleeding.

After the clip unit 1 has left, the clip manipulating device 5 is removed from the inside of the forceps channel.

In most cases, in the ligation of a physiological tissue due to the clipping apparatus, the ligation of a plurality of clips 2 is often continuously carried out, and a next clip unit 1 is often attached immediately after removal. In the present embodiment, in the case of mounting a second and subsequent clip units 1, the clip manipulating device 5 is removed from an endoscope channel, and then, the slider 11 is pushed out against the tip end side, whereby the hook 12 is extruded from the coil sheath 7. At this time, the link member 3 of the first clip unit 1 is left to be engaged with the hook section 12c.

Figure 6:
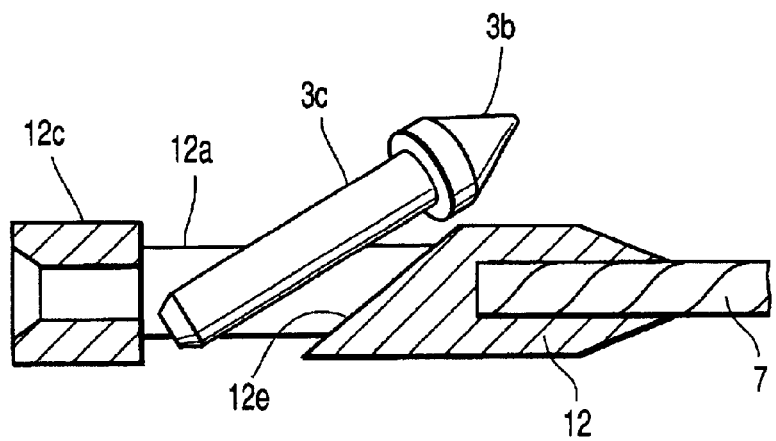
FIG. 6 is a view illustrating an operation of the illustrative embodiment according to the present invention, and is a longitudinal side view showing a relationship between the stop tube and the link member.

In this state, the link member 3 of a second clip unit 1 is pushed at the tip end side of the hook section 12 as is. Then, the first link member 3 left at the hook section 12 is pushed by a second link member 3, and is pushed against the proximal end side of the hook section 12. Then, the proximal end part of the first link member 3 abuts against the inclined face 12e at the proximal end side of the hook section 12. As shown in FIG. 6, the abutting part moves along the inclined face 12e, is pushed out of a space between the elastic arms 12a and 12b, and slips out of the hook section 12c. In this way, the removal of the first link member 3 and the mount of the second clip unit 1 are completed at the same time. Then, the ligation and mounting of the clip 2 can be continuously carried out similarly.

According to the first embodiment described previously, the clip manipulating device 5 of the clip unit 1 can be mounted on the hook section 12 merely by pushing the clip unit 1 against the hook section 12. Even if a hand is then released, the mounted device does not slip off due to the pinch force of the hook section 12, thus making mounting simple and reliable.

In addition, the subsequent housing or releasing of the clip unit 1 into or from the sheath section 6 or the ligation of the clip unit 1 can be carried out by manipulating only the slider 11 to be advanced and retracted. In addition, in remounting the clip 2, the link member 3 can be removed at the same time when the clip 2 is mounted, thus making simplified operation and making it possible to complete treatment within a short period of time.

Further, when the clip unit 1 is pulled out of the sheath section 6, the slider 11 is pressed. When the clip unit 1 is ligated, the slider 11 is pulled. In this way, the advancing and retracting direction of the clip unit 1 is coincident with that of the slider 11, and an operator can make operation that is intuitively understandable, thus reducing the possibility of making incorrect operation.

Furthermore, the clip manipulating device 5 can be easily processed and assembled, and can be processed and assembled inexpensively because of its simple construction.

Figure 7A:
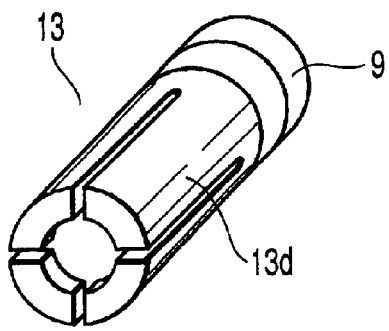
FIG. 7A shows a second embodiment according to the present invention, and is a perspective view of a coil pipe.
Figure 7B:
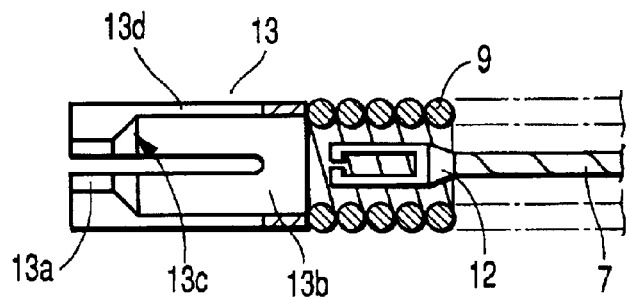
FIG. 7B is a longitudinally sectional side view of the second embodiment.
Figure 8:
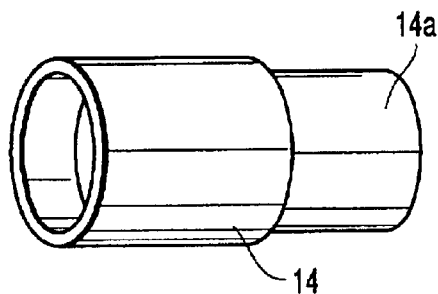
FIG. 8 is a perspective view of a stop tube according to the illustrative embodiment.

FIG. 7A, FIG. 7B, and FIG. 8 each show a second embodiment according to the present invention. The present embodiment is identical to the first embodiment in configuration except the stop tube 4 of the clip unit 1 and the coil pipe 8 of the clip manipulating device 5 according to the first embodiment.

A coil pipe 13 according to the second embodiment is molded by processing a resilient metal pipe. The coil pipe 13 is formed in a substantially cylindrical shape as shown in FIG. 7A and FIG. 7B, where a small diameter section 13a whose inner diameter is small is provided at its tip end side, and a large diameter section 13b is provided at its proximal end. Further, an inclined section 13c is provided between the small diameter section 13a and the large diameter section 13b. Furthermore, at the coil pipe 13, as shown in FIG. 7A, four slits are provided at its tip end side, and an arm section 13d between the respective slits is elastically deformed so that the diameter of the small diameter section 13a can be expanded/contracted.

A stop tube 14 of the clip unit 1 as shown in FIG. 8, has an outer diameter greater than the inner diameter of the small diameter section 13a of the coil pipe 13, and is formed in a substantial pipe shape smaller than the inner diameter of the large diameter section 13b. In addition, an engagement section 14a smaller than the inner diameter of the small diameter section 13a of the coil pipe 13 is provided at the proximal end side.

Now, an operation of the second embodiment will be described here. In order to mount the clip unit 1 on the clip manipulating device 5, as in the first embodiment, the slider 11 is pushed out against the tip end side; the hook section 12 is extruded from the coil pipe 13, and the link member 3 of the clip unit 1 is pushed against the hook section 12 to be pinched and fixed. Then, the arm section 13d of the coil pipe 13 is elastically deformed in the outer periphery direction. While the small diameter section 13a of the coil pipe 13 is opened to have a diameter greater than the outer diameter of the stop tube 14, the slider 11 is pulled toward the proximal end, and the hook section 12 and the clip unit 1 are pulled into the sheath section 6.

In this state, as in the first embodiment, the sheath section 6 is guided to a target site via an endoscope. Next, the slider 11 is manipulated to be pushed out against the tip end side again, whereby the clip unit 1 is extruded from the sheath section 6. At this time, the inclined section 13c of the coil pipe 13 is pushed at the clip unit 1, and the arm section 13d of the coil pipe 13 is deformed in the outer periphery direction. Then, the small diameter section 13a is opened to be greater than the outer diameter of the stop tube 14 of the clip unit 1, thus making it possible to extrude the clip unit 1 to the outside from the sheath section 6.

When the clip unit 1 is extruded to an extent such that the engagement section 14a of the stop tube 14 passes through the small diameter section 13a of the coil pipe 13, the arm section 13d of the coil pipe 13 is elastically restored, and the small diameter section 13a of the coil pipe 13 is contracted to its original diameter.

When the slider 11 is pulled into the proximal end side again, the small diameter section 13a of the coil pipe 13 is engaged with the engagement section 14a of the stop tube 14. Then, a step at the tip end part of the engagement section 14a abuts against the tip end face of the coil pipe 13, and the stop tube 14 and the coil pipe 13 are fixed at a predetermined position. Thereafter, the clip can be ligated as in the first embodiment. Advantageous effect of the second embodiment is identical to that of the first embodiment. A duplicate description is omitted here.

FIG. 9A, FIG. 9B, FIG. 10A, and FIG. 10B each show a third embodiment according to the present invention. The present embodiment relates to a method of fixing the clip unit 1 to the clip manipulating device 5 according to the first embodiment. These embodiments are identical to each other except that the link member 3 of the clip unit 1 and the hook section 12 of the clip manipulating device 5 are shaped differently.

Figure 9A:
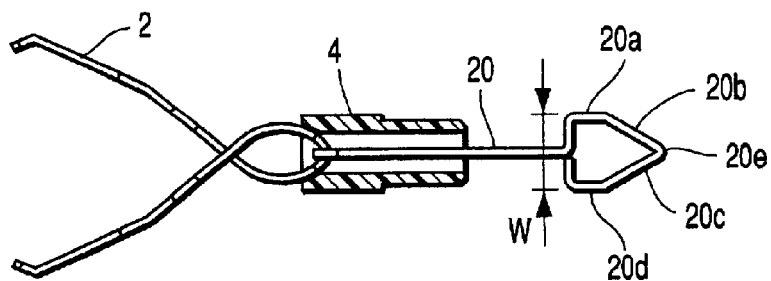
FIG. 9A shows a third embodiment according to the present invention, and is a longitudinal side face of a clip unit and a clip manipulating device.
Figure 9B:
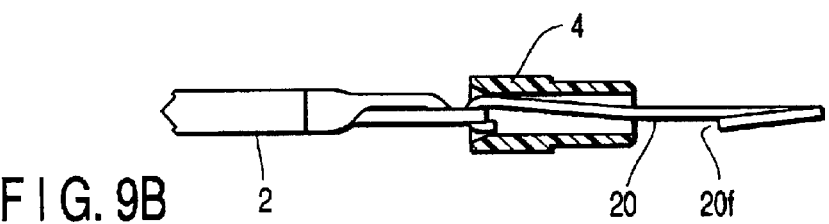
FIG. 9B is a longitudinally plan view of the same.
Figure 10A:
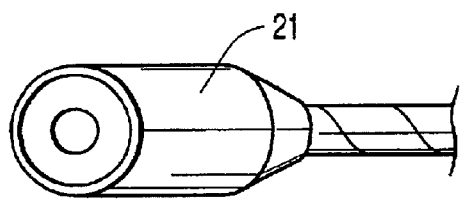
FIG. 10A shows the illustrative embodiment according to the present invention, and is a perspective view of a hook section.
Figure 10B:
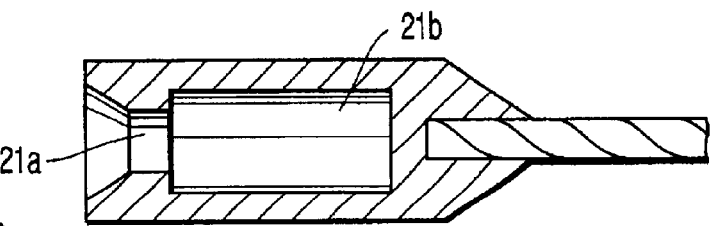
FIG. 10B is a longitudinal side view of the illustrative embodiment.

In the third embodiment, as shown in FIG. 9A, a link member 20 is formed by bending a metal wire. The proximal end side of the link member 20 is bent in a pentagonal shape having sides 20a, 20b, 20c, and 29d and an apex 20e. Further, as shown in FIG. 9B, a proximal end part 20f of the link member 20 is bent and molded by vertically shifting it. In addition, a hook section 21 is formed in a hollow pipe shape, as shown in FIG. 10A. As shown in FIG. 10B, there are provided: a large diameter section 21b having an inner diameter greater than a width W (refer to FIG. 9A) of a pentagon shaped bent section of the link member 20; and a small diameter section 21a having an inner diameter smaller than the width W.

Now, an operation of the third embodiment will be described here. When the link member 20 is pushed at the tip end side of the hook section 21, the sides 20b and 20c of the pentagon shaped bent section of the link member 21 abuts against the tip end part of the small diameter section 21a of the hook section 21. Then, the abutting sides are elastically deformed and reduced around the apex 20e of the pentagon shaped bent section to an extent such that the width W between the sides 20a and 20d is smaller than the diameter of the small diameter section 21a. When the link member 20 is further pushed, the pentagon shaped bent section passes through the small diameter section 21a, and is restored in the large diameter section 21b. Then, the restored section is engagingly fixed to a step between the small diameter section 21a and the large diameter section 21b.

Other operations and advantageous effects of the third embodiment are identical to those of the first embodiment. A duplicate description is omitted here.

FIG. 11A to FIG. 11C and FIG. 12 each show a fourth embodiment according to the present invention. The present embodiment relates to a method of fixing the clip unit 1 to the clip manipulating device 5 according to the first embodiment. These embodiments are identical to each other in configuration except that the link member 3 of the clip unit 1 and the hook section 12 of the clip manipulating device 5 are shaped differently.

Figure 11A:
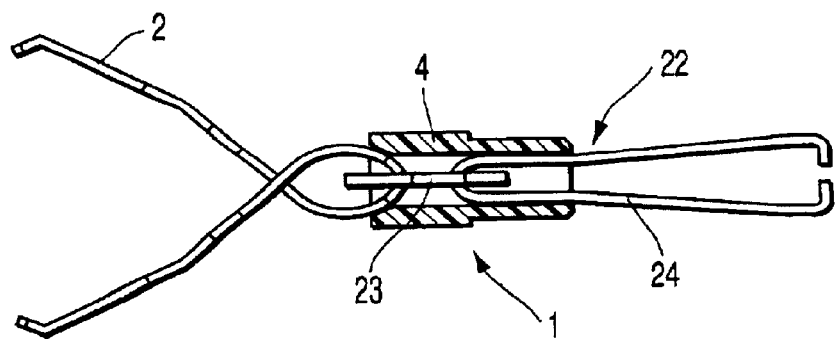
FIG. 11A to FIG. 11C each show a fourth embodiment of the present invention, where

In the fourth embodiment, as shown in FIG. 11A, a link member 22 is composed of a first link member 23 processed from a metal plate material and a second link member 24 obtained by bending and molding a metal plate material such as a plate spring material.

Figure 11B:
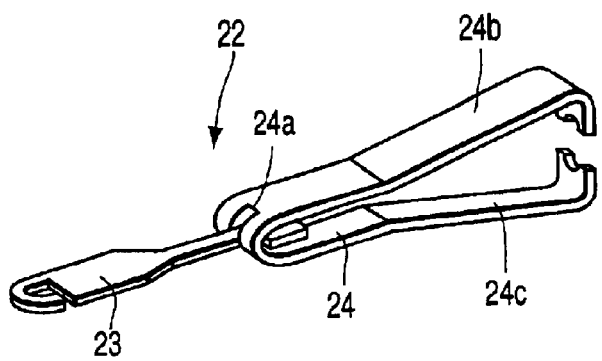
Figure 11C:
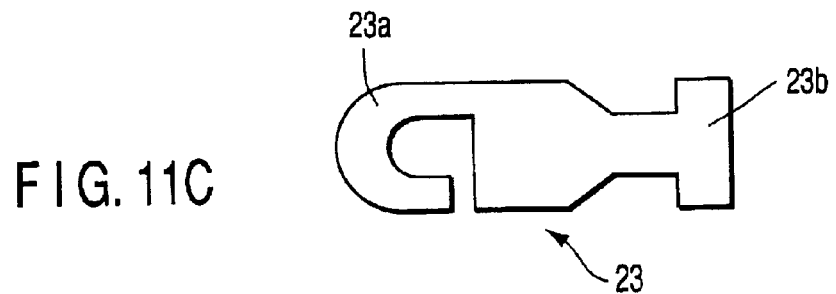
Figure 12:
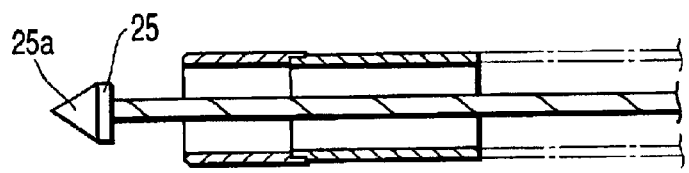
FIG. 12 shows the illustrative embodiment according to the present invention, and is a side view of a hook section.

As shown in FIG. 11C, a claw shaped claw hook 23a is provided at a tip end side of the first link member 23 so as to be engaged with the clip 2. In addition, a T-shaped T hook 23b is provided to be fixed to the second link member at the proximal end side of the first link member 23. At the second link member 24, as shown in FIG. 11B, there are provided: a slit section 24a to be fixed to the first link member 23; and arm sections 24b and 24c having closing properties, the arm sections being fixed to the hook section 25. The hook section 25 is formed in a cone shape having an inclined face 25a at its tip end side as shown in FIG. 12.

Now, an operation of the fourth embodiment will be described here. When the link member 22 is pushed at the tip end side of the hook section 25, the ends of the arm sections 24b and 24c of the second link member 24 abut against the inclined face 25a of the hook section 25, and the arm sections 24b and 24c are elastically deformed and opened along the inclined face 25a. When the link member 22 is further pushed, the arm sections 24b and 24c are closed, and the link member 22 is engagingly fixed to the hook section 25.

Otherwise, operation and advantageous effect of the fourth embodiment are identical to those of the first embodiment. A duplicate description is omitted here.

Figure 13A:
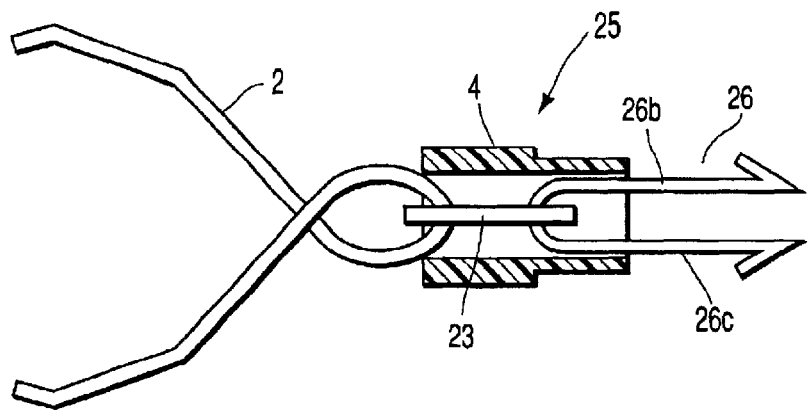
Figure 13B:
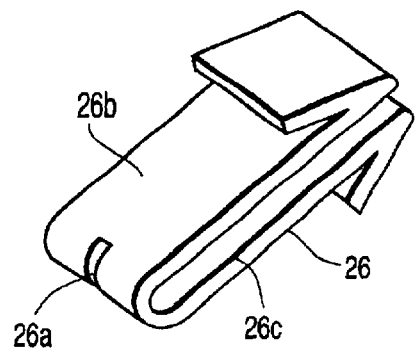

FIG. 13A and FIG. 13B each show a fifth embodiment according to the present invention. The present embodiment relates to a method of fixing the clip unit 1 to the clip unit 5 according to the first embodiment. These embodiments are identical to each other in configuration except that the link member 3 of the clip unit 1 is different.

In the fifth embodiment, as shown in FIG. 13A, the link member 25 is composed of the previously described first link member 23 and a second link member 26 obtained by bending and molding a metal plate member such as a plate spring.

The second link member 26 is bent at both ends of the plate material at an acute angle, and further, is bent in a semi-circular shape at the center of the plate material, whereby arm sections 26b and 26c are molded. In addition, a slit section 26a to be fixed to the first link member 23 is provided in the same way as the link member 24 according to the fourth embodiment.

Now, an operation of the fifth embodiment will be described here. When the link member 25 is pushed at the tip end side of the hook section 12, an end of the second link member 26 abuts against the inclined face 12e of the hook section 12. The elastic arms 12a and 12b of the hook section 12 are elastically opened, and the arm sections 26b and 26c of the second link member 26 are elastically closed. Then, when the link member 25 is further pushed, where the end of the second link member 26 passes through the pinch sections 12c and 12d of the hook section 12, the elastic arms 12a and 12b and the arm sections 26b and 26c are restored, and are engagingly fixed.

According to the present embodiment, both of the hook section 12 and the second link member 26 are structured to be elastically deformed and restored, whereby a deformation quantity of both of these members can be reduced. Thus, the elastic arm sections 12a and 12b can be reduced in length, and an amount of advancing and retracting force of the hook section 12 can be reduced. In addition, the elastic arms 12a and 12b are reduced in length, and the strength can be increased.

Other operations and advantageous effects of the fifth embodiment are identical to those of the first embodiment. A duplicate description will be omitted here.

Figure 14:
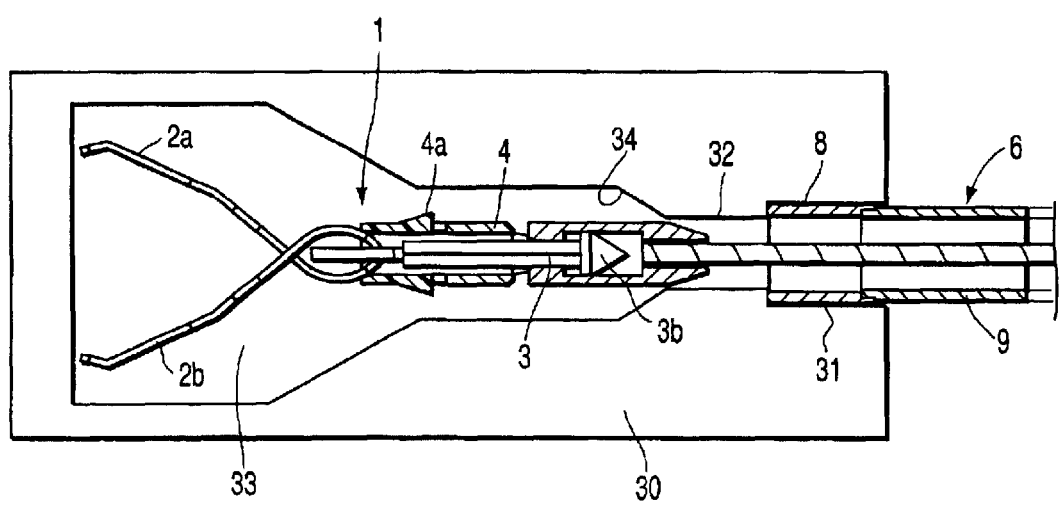
FIG. 14 shows a sixth embodiment according to the present invention, and is a longitudinal side view of a clip unit.

FIG. 14 shows a sixth embodiment according to the present invention. The present embodiment is composed of a clip unit 1 and a clip case 30, as shown in FIG. 14. The clip case 30 is manufactured by molding a resin with its good smoothness such as polyacetal. A large diameter hole 31 greater than an outer diameter of a coil pipe 8 of a clip manipulating device 5 is provided at the clip case 30. The clip unit 1 is housed in the clip case 30 so that an arrowhead hook 3b of a link member 3 of the clip unit 1 orients the large diameter hole 31.

In the clip case 30, a small diameter section 32 that is smaller than an inner diameter of the coil pipe 8 and greater than an external dimension of a stop tube 4 are provided more deeply of the large diameter hole 31. In addition, an inclined section 34 is provided between a housing section 33 having the clip unit 1 housed therein and the small diameter section 32. This inclined section 34 is provided in order to reduce a protrusion 4a of the previously stop tube 4 when the clip unit 1 is pulled out of the clip case 30. In order to smoothly reduce this protrusion 4a, it is desirable that the inclined section 34 be set at an angle of 30 degrees or less.

Now, an operation of the sixth embodiment will be described here. As shown in FIG. 14, while the coil pipe 8 is inserted into the large diameter hole 31 of the clip case 30, the slider 11 is manipulated to be pushed out against the tip end side, whereby the hook section 12 is extruded into the clip case 30. Then, the arrowhead hook 3b of the link member 3 is pinched and fixed to the hook section 12 in the same way as in the first embodiment.

At this time, the coil pipe 8 and clip unit 1 are fixed at their predetermined positions by the clip case 30, and thus, the hook section 12 abuts against the link member 3 straight. Because of this, the mounting of the hook section 12 and the link member 3 is reliably carried out without a need for positioning in particular. When the slider 11 is then pulled toward the proximal end side, the clip unit 1 pinched and fixed to the hook section 12 as well is pulled toward the proximal end side, and is pulled toward the large diameter hole 31 of the clip case 30. At this time, the protrusion 4b of the stop tube 4 abuts against the inclined face 34 of the clip case 30, is elastically deformed along the inclined face 34, and is pushed into the stop tube 4.

Figure 3C:
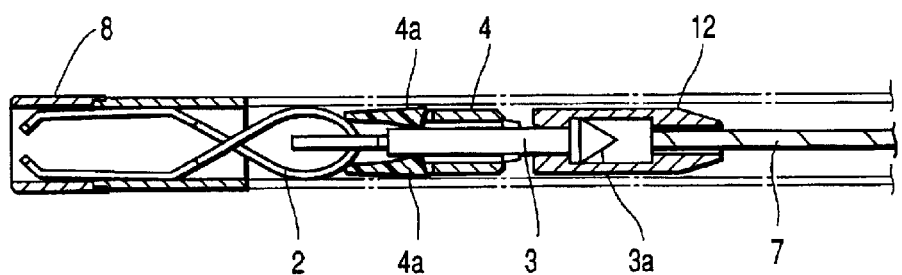

Then, the clip unit 1 is pulled into the sheath section 6 of the clip manipulating device 5 through the small diameter section 32 of the clip case 30. At this time, the protrusion 4a of the stop tube 4 comes into contact with an inner face of the small diameter section 32 of the clip case 30, and is pushed into the stop tube 4. Thus, the clip unit 1 is pulled into a coil sheath 9 without being caught by an end face of the coil pipe 8. Further, the arm sections 2a and 2b of the clip unit 1 each are closed along the inclined section 34, and thus, the clip unit 1 is smoothly housed in the sheath section 6 as shown in FIG. 3C.

According to the present embodiment, the mounting between the clip unit 1 and clip manipulating device 5 is completed merely by inserting the sheath section 6 of the clip manipulating device 5 into the large diameter hole of the clip case 30, and then, advancing and retracting the slider 11 forward and backward once. The work of positioning the hook section 12 and the link member 3 and of pushing the protrusion 4a of the stop tube 4 are eliminated, and thus, preparation for the clipping apparatus is simpler and more reliable. Other operations and advantageous effects are identical to those of the first embodiment. A duplicate description is omitted here.

Figure 15A:
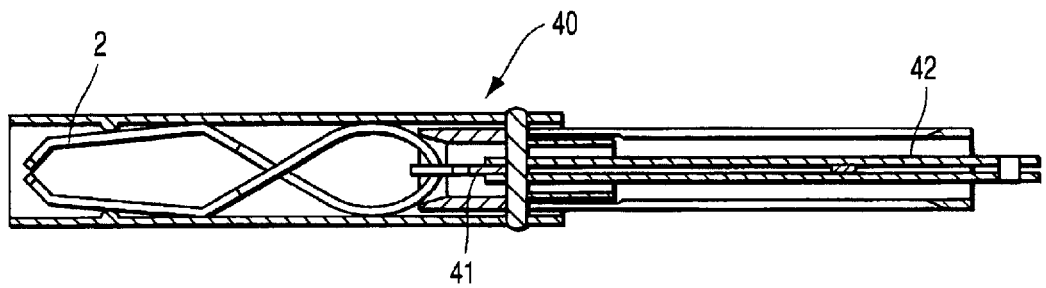
FIG. 15A to FIG. 15C each show a seventh embodiment according to the present invention, where
Figure 15B:
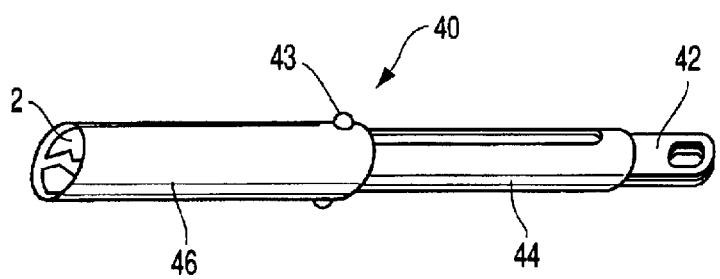
Figure 15C:
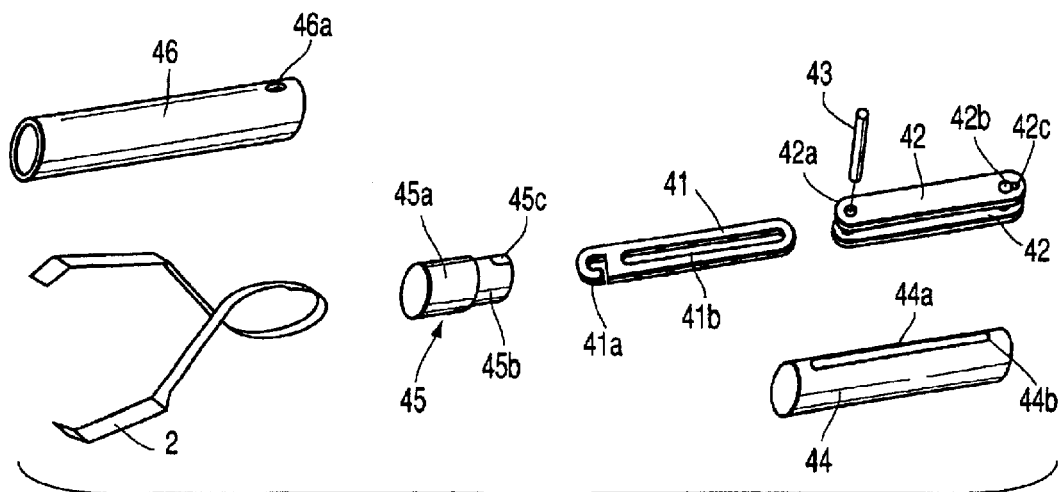
Figure 16:
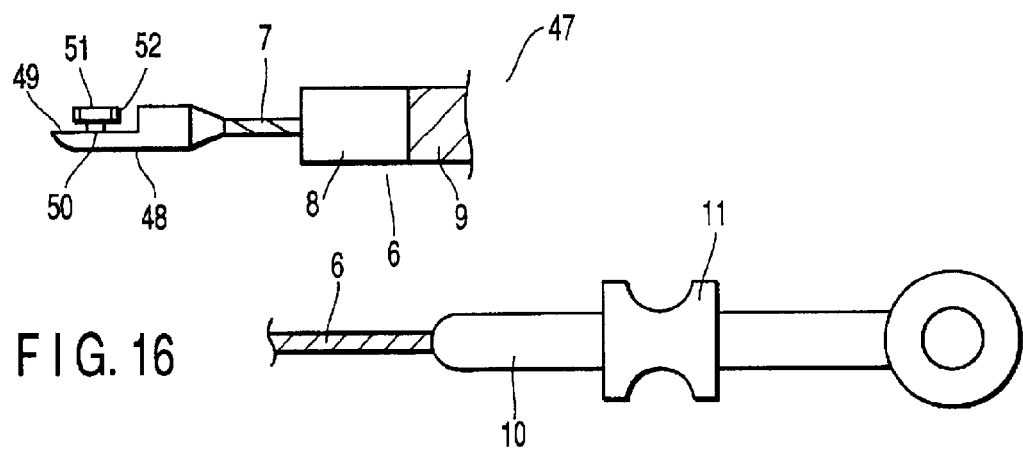
FIG. 16 is a side view of a clip manipulating device according to the illustrative embodiment.

FIG. 15A to FIG. 17C each show a seventh embodiment according to the present embodiment. A clipping apparatus according to the present embodiment is composed of a clip unit 40 a shown in FIG. 15A and FIG. 15B and a clip manipulating device 47 as shown in FIG. 16.

The clip unit 40 has a clip 2, a link member 41, a pair of slide plates 42, a slide bar 43, a link pipe 44, a stop tube 45 as a tightening ring, and a clip cover 46 that houses the clip 2. The clip 2 is shaped in the completely same way as the clip 2 according to the first embodiment.

The link member 41 is molded by photo-etching or press-processing a metal plate material. A claw shaped claw hook 41a is formed at a tip end part of this link member 41 as shown in FIG. 15. This claw hook 41a hooks an end part 2c at the proximal end side of the clip 2 so as to removably engage the clip 2. Further, a slit section 41b for penetrating the slide bar 43 described later is provided at the link member 41.

The slide bar 43 is manufactured by molding a material with its certain flexibility such as a resin, the material being capable of being cut. The slide bar 43 has an outer diameter capable of passing through a small hole 42a of the slide plate 42 described later, a slit section 45c of the stop tube 45, a slit section 44a of the link pipe 44, and a small hole 46a of the clip cover 46, and is formed in a cylindrical shape having a length that is slightly greater than an outer diameter of the clip cover 46.

The slide plate 42 is molded by photo-etching and press-processing a metal plate material in the same was as in the link member 41. The small hole 42a for passing the slide bar 43, the large diameter hole 42b to be linked with the clip manipulating device 47, and the small diameter hole 42c disposed so as to communicate with the large diameter hole 42b are provided at the slide plate 42 in the same way as in the slit section 41b of the link member 41.

The stop tube 45 is made of a substantially cylindrical shape, and an outer diameter of the stop tube 45 is composed of a large diameter section 45a at a tip end side and a small diameter section 45b at a proximal end side. Further, the slit section 45c passing the slide bar 43 is provided at the stop tube 45 in the same way as in the slit section 41b of the link member 41.

The link pipe 44 for linking between the stop tube 45 and the clip manipulating device 47 is formed in a substantially cylindrical shape, and a slit section 44a for passing the slide bar 43 is provided in the same way as in the slit section 41b of the link member 41. A blade 44b for cutting a slide bar 15 is provided at proximal end part of the slit section 44a.

The clip cover 46 for housing the clip 2 is manufactured by molding a material having its proper flexibility such as Teflon or polyethylene in a cylindrical shape having an inner diameter capable of housing the clip 2. A small hole 46a for passing the slide bar 43 is provided at the clip cover 46 in the same way as in the slit section 41b of the link member 41.

Therefore, in order to fabricate the clip unit 1 in the state shown in FIG. 15A and FIG. 15B, first, while the claw hook 41a of the link member 41 is engaged with the end part 2c at the proximal end side of the clip 2, the stop tube 45 is engaged with the link member 41 until abutment against the end part 2c at the proximal end side of the clip 2 has been obtained. Further, while the link member 41 is pinched between the pair of slide plates 42 at a position at which the small hole 42a of the slide plate 42 is coincident with the tip end part of the slit section 41a of the link member 41, the link pipe 44 is engaged with the link member 41, the pair of slide plates 42, and the small diameter section 45b of the stop tube 45 until the tip end part of the slit section 44a of the link pipe 44 is coincident with the tip end part of the slit section 45c.

In this state, while the clip cover 46 is further engaged with the clip 2 until the small hole 46a of the clip cover 46 has been coincident with the tip end part of the slit section 44a of the link pipe 44, the slide bar 43 is further passed through the small hole 46a of the clip cover 46, the slit section 44a of the link pipe 44, the slit section 45c of the stop tube 45, the small hole 42a of the slide plate 42, and the slit section 41b of the link member 41, whereby the slide plate 42 and clip cover 46 are linked with each other to be slidably mounted to the link member 41 and the link pipe 44 so that the clip unit 40 can be assembled in a state as shown in FIG. 15A and FIG. 15B.

A configuration of the clip manipulating device 47 is identical to that of another element except that the hook section 12 of the clip manipulating device 5 according to the first embodiment is different. At a hook section 48 of the clip manipulating device 47 according to the present embodiment, a recessed cutout 49 is formed at the tip end side of a bar shaped element as shown in FIG. 16. On a bottom face of this cutout 49, a pin 50 is protruded vertical to the advancing and retracting direction of a manipulating wire 7. A circular head 51 and a small diameter section 52 smaller than this head 51 in diameter are molded at this pin 50. The head 51 of the pin 50 is smaller than the large diameter hole 42b of the slide plate 42 shown in FIG. 15C, and is greater than the small diameter hole 42c. Further, the small diameter section 52a of the pin 50 is smaller than the small diameter section 42c of the slide plate 42 in dimensions.

Figure 17A:
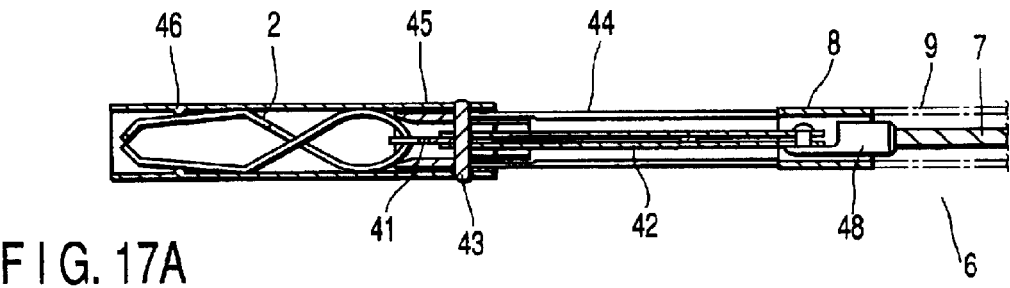
FIG. 17A to FIG. 17C each illustrate an operation of the illustrative embodiment, wherein a clip unit is connected to a clip manipulating device.

Now, an operation of the seventh embodiment will be described here. As shown in FIG. 17A, in order to mount the clip unit 40 on the clip manipulating device 47, first, the slider 11 is manipulated to be pushed out against the tip end side, whereby the hook section 48 is extruded into the coil pipe 8.

Then, the hook section 48 is engaged with the large diameter section 42b of the slide plate 42 of the clip unit 40, and thereafter, the entire clip unit 40 is pulled toward the tip end side.

Then, the head 51 of the pin 50 is engaged with the small diameter section 42c of the slide plate 42. The slider 11 is manipulated to be pulled into the proximal end side, whereby the hook section 48 is pulled into the sheath section 6, the link pipe 44 abuts against the coil pipe 8, and the mounting of the clip unit 40 is completed.

The clip 2 of the clip unit 40 is housed in advance in the clip cover 46, and thus, the clip unit 40 is introduced into a cavity via a forceps channel of an endoscope, whereby the clip unit can be guided to a target site.

Next, when the slider 11 is pulled toward the proximal end side, thereby pulling the manipulating wire 7 to be retracted to the proximal end side, the slide plate 42 and the slide bar 43 passed through the small hole 42a of the slide plate 42 is pulled. The slide bar 43 passes through the small hole 46a of the clip cover 46. Thus, the slide bar 43 is pulled, whereby the clip cover 46 as well is pulled toward the proximal end side, and the clip 2 is protruded from the clip cover 46.

Figure 17B:
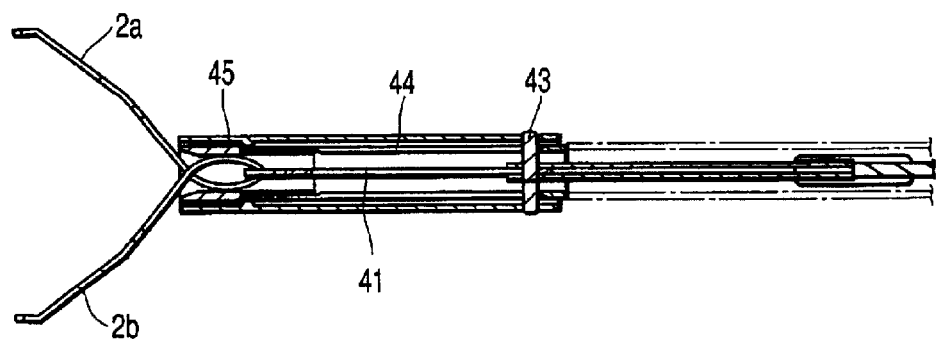
Figure 17C:
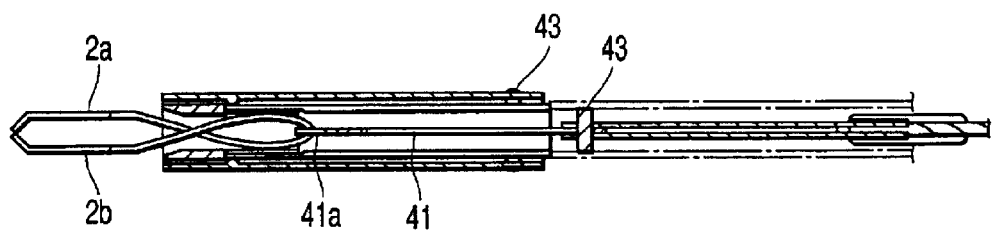

At this time, the link member 41 is maintained as is without being pulled toward the proximal end side because the slide bar 43 slides on the slit section 41b. When the slider 11 is further pulled toward the proximal end side, the slide bar 43 abuts against the proximal end part of the slide section 41b of the link member 41, and the link member 41 as well is pulled toward the proximal end side. Then, the end part 2c at the proximal end side of the clip 2 is crashed by being pulled into the stop tube 14, and the arm sections 2a and 2b are opened significantly in the outward direction, as shown in FIG. 17B.

In this state, as is the case with the first embodiment, the arm sections are guided to a target physiological tissue, and further, the slider 11 is pulled toward the proximal end side. Then, the slider bar 43 abuts against the proximal end part of the slit section 44a of the link pipe 44. When the slider 11 is further pulled toward the proximal end side, the slide bar 43 is cut by the blade 44b provided at the proximal end part of the slide section 44a, and the slide bar 43 is released from the clip cover 46. When the slider 11 is continuously pulled as is, the arm sections 2a and 2b of the clip 2 are pulled onto the stop tube 45. Then, the arm sections 2a and 2b are closed, and a target tissue is pinched between these arm sections. In this state, the slider 11 is further pulled toward the proximal end side, whereby the claw hook 41a of the link member 41 is deformed and expanded. Then, the clip 2 is disengaged from the link member 41, is released from the clip manipulating device 47, and is left in a body while the physiological tissue is pinched.

The advantageous effect of the seventh embodiment is as follows. That is, the clip 2 is housed in advance in the clip cover 46. The slider 11 is advanced and retracted, whereby the forceps channel of the endoscope can be inserted immediately after mounting the clip unit 1, thus simplifying preparation. In addition, in ligating the clip unit 1 as well, the clip unit 1 is protruded from the clip cover 46 merely by pulling the slider 11, and ligation can be carried out as is, thus simplifying operation.

In addition, a structure is provided such that the slide car 43 is cut, whereby a length of the slit section 44a of the link pipe 44 is equal to a retraction length of the clip cover 46. Thus, the entire length of the clip unit 40 can be reduced, and the properties of passing into a forceps channel is improved.

Further, the clip manipulating device 5 can be easily processed and assembled, and can be processed and assembled inexpensively because of its simple construction.

Figure 18A:
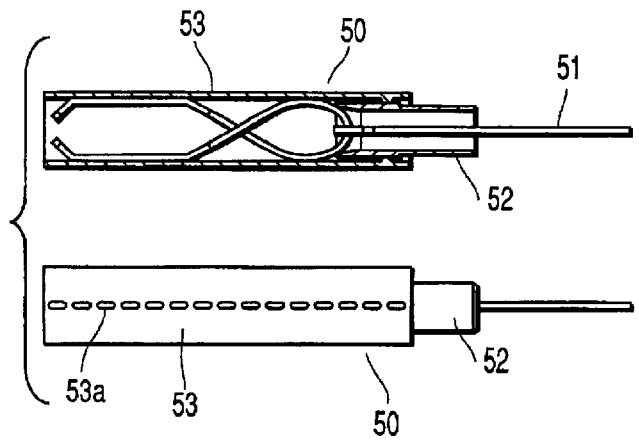
FIG. 18A to FIG. 18C each show an eighth embodiment according to the present embodiment, where
Figure 18B:
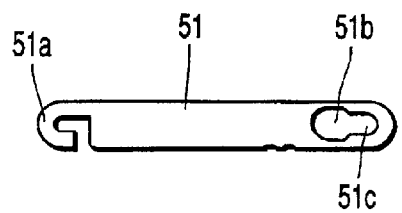
Figure 18C:
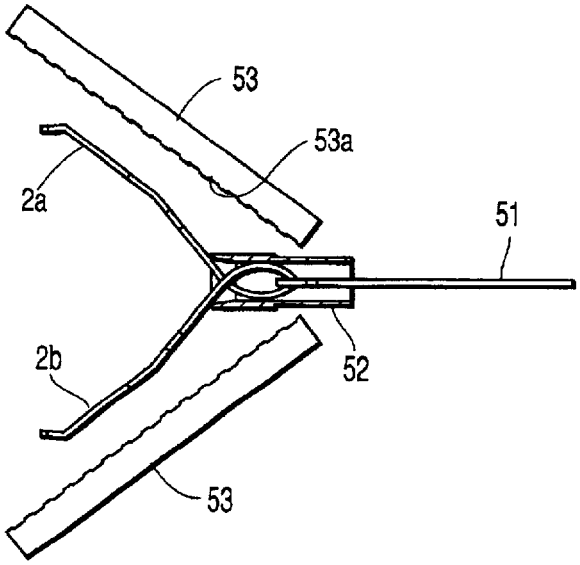
Figure 19D:
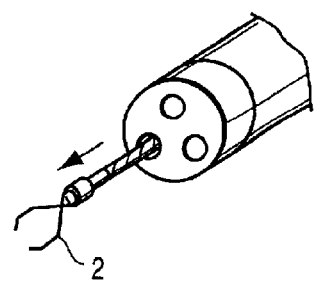

FIG. 18A to FIG. 18C each show an eighth embodiment according to the present invention. A clipping apparatus according to the present embodiment is composed of a clip unit 50 shown in FIG. 18A to FIG. 18C and a clip manipulating device 47 that is identical to that according to the seventh embodiment. The clip unit 50 is composed of: a clip 2 formed in the completely identical shape to that of the first embodiment; a link member 51 as a link member; a stop tube 52 of a clip tightening ring; and a clip cover 53.

At a tip end part of the link member 51, as shown in FIG. 18B, a claw shaped claw hook 51a is formed so as to be engaged with the end part 2c at the proximal end side of the clip 2. On the other hand, at the proximal end side of the link member 51, as in the proximal end side of the slide plate 42 according to the seventh embodiment, the large diameter hole 51b and small diameter hole 51c are provided so as to be removably engaged with the clip manipulating device 47.

The clip cover 53 is molded by a material to be easily torn such as paper, for example, and is engaged in advance with the clip unit 5 while the clip 2 is closed shown in FIG. 18A. A snapaway perforation 53a is provided at both sides of a side face of the clip cover 53.

The clip unit 50 is mounted on the clip manipulating device 47, and is introduced into a cavity in the same way as in the seventh embodiment. After the clip unit has entered the cavity, when the slider 11 is pulled toward the proximal end side, the arm sections 2a and 2b of the clip 2 are opened significantly in an outward direction. At this time, the clip cover 53 breaks and snaps-open along the perforation 53a, as shown in FIG. 18C so that a target site can be ligated by the arm sections 2a and 2b of the clip 2.

Other operations and advantageous effects are similar to those of the seventh embodiment. A duplicate description is omitted here.

FIG. 19A to FIG. 19D each show a ninth embodiment according to the present invention. A clipping apparatus according to the present embodiment is composed of: a clip unit 50 and a clip cover 54 shown in FIG. 19A; and the previously described clip manipulation device 47.

Figure 19A:
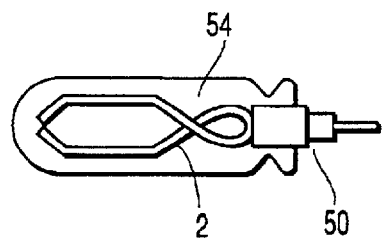

The clip cover 54 is fabricated by molding a soft resin such as silicon, for example, and is covered in advance on the clip unit 50 while the clip 2 is opened, as shown in FIG. 19A. The clip cover 54 is formed in a substantially cylindrical shape having an external diameter that is slightly greater than a forceps channel of an endoscope, and is closed at a tip end side. In addition, the outer surface at the tip end side is formed in a spherical shape in consideration of endoscope insert properties.

The clip unit 50 is mounted on the clip manipulating device 47, and is introduced into a cavity in the same manner as in the seventh embodiment.

Figure 19B:
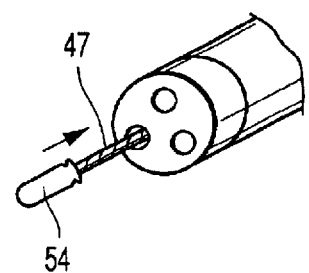
Figure 19C:
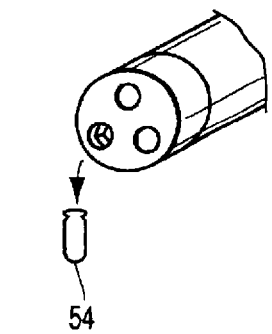

After the clip unit has been introduced into the endoscope, the clip unit 50 and clip cover 54 are projected from the forceps channel of the endoscope into the cavity as shown in FIG. 19B. In this state, the entirety of the clip manipulating device 47 is pulled toward the proximal end side. Then, the clip unit 50 is pulled into the forceps channel of the endoscope. At this time, the clip cover 54 is caught into a tip end face of the forceps of the endoscope as shown in FIG. 19, and slips out of the clip unit 50. In this state, the entirety of the clip manipulating device 47 is pushed out again against the tip end side, whereby the clip unit 50 can be ligated.

Other operations and advantageous effects are identical to those according to the seventh embodiment. A duplicate description is omitted here.

Figure 20A:
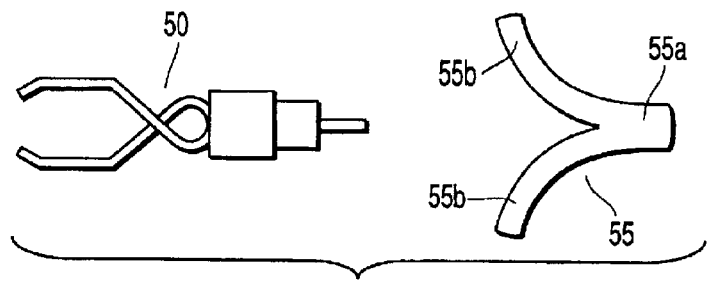
FIG. 20A to FIG. 20C each show a tenth embodiment according to the present invention, where
Figure 20B:
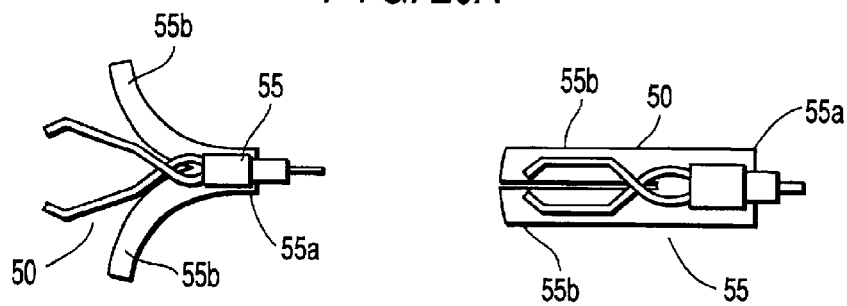
Figure 20C:
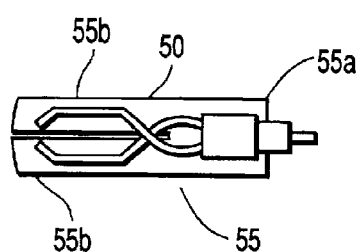

FIG. 20A to FIG. 20 each show a tenth embodiment according to the present invention. A clipping apparatus according to the present embodiment is composed of: a clip unit 50, a clip cover 55, and the previously described clip manipulating device 47 as shown in FIG. 20A.

The clip cover 55 is fabricated by molding a resin having proper flexibility such as Teflon, for example. At the clip cover 55, as shown in FIG. 20A, there are provided: a cylindrical fixing section 55a having an outer diameter slightly smaller than that of a stop tube 52 of the clip unit 50; and a cover section 55b having a semi-cylindrical cross section, the cover section being greatly opened at the tip end side. The clip cover 55 is fixed to be pressed into the stop tube 52 of the clip unit 50 while the cover is engaged with the stop tube 52, as shown in FIG. 20B.

The clip unit 50 is mounted on the clip manipulating device 47 in the same manner as in the seventh embodiment.

After the clip unit has been mounted, as shown in FIG. 20, while the cover section 55b of the clip cover 55 is closed so as to engage the arm sections 2a and 2b of the clip 2 of the clip unit 50, the clip unit 50 is inserted into the forceps channel of the endoscope, and is introduced into a cavity. After the clip unit 50 has been introduced, when the clip unit 50 is protruded from the forceps channel, the cover section 55b of the clip cover 55 is molded in an opened shape, and thus, is automatically opened, whereby the clip unit 50 can be ligated.

The other operation and advantageous effect are identical to those according to the seventh embodiment. A duplicate description is omitted here.

Figure 21:
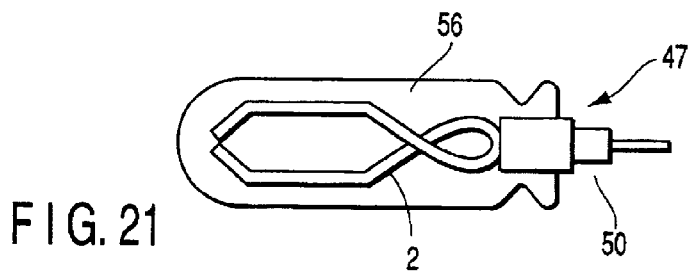
FIG. 21 shows an eleventh embodiment according to the present invention, and is a side view of a clip unit and a clip cover.

FIG. 21 shows an eleventh embodiment according to the present invention. A clipping apparatus according to the present embodiment is composed of: a clip unit 50; a clip cover 56; and the previously described clip manipulating device 47 as shown in FIG. 21.

The clip cover 56 is fabricated by molding a material such as oblate, which is dissolved when the cover comes into contact with water. The clip cover 56 is engaged in advance with the clip unit 50 while the clip 2 is closed as shown in FIG. 21, and is formed in a substantially cylindrical shape having an outer diameter smaller than the forceps channel of the endoscope.

The clip unit 50 is mounted on the clip manipulating device 47, and is introduced into a body in the same manner as in the seventh embodiment. After the clip unit 50 has been introduced, the clip cover 56 is dissolved when the cover comes into contact with the water content in the cavity so that the clip unit 50 can be ligated. In addition, when the water content in the cavity is small in amount, water is fed to the forceps channel so that the clip cover 56 can be dissolved.

Other operations and advantageous effects are identical to those according to the seventh embodiment. A duplicate description is omitted here.

Figure 22A:
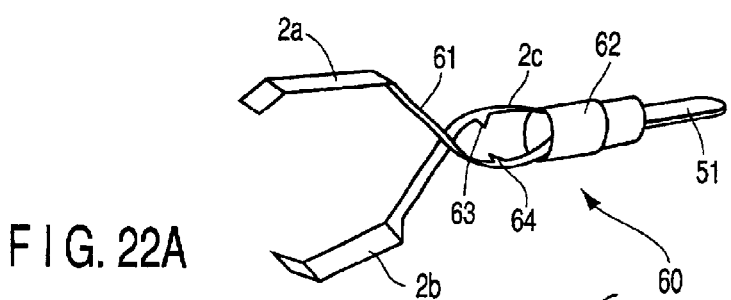
FIG. 22A to FIG. 22C each show a twelfth embodiment according to the present invention, where
Figures 22B, 22C:
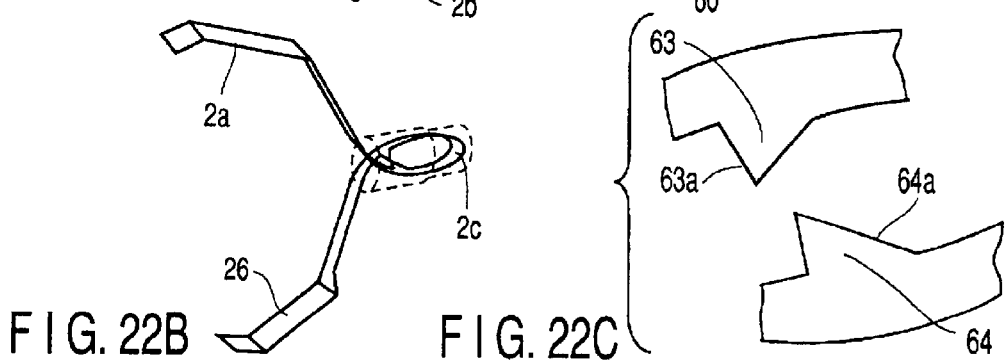

FIG. 22A to FIG. 22C each show a twelfth embodiment according to the present invention. As shown in FIG. 22A, a clip unit 60 is composed of: a clip 61; a stop tube 62 for closing the clip 61 by being engagingly mounted on the clip 61; and the previously described link member 51.

The clip 61 is formed in a shape substantially similar to the clip 2 shown in the first embodiment. As shown in FIG. 22A, there are provided: arm sections 2a and 2b; a substantially circular proximal end 2c; and protrusions 63 and 64 of 0.3 mm to 0.5 mm in height in parallel to a plate face of a base material between the arm sections 2a and 2b each and the proximal end 2c. The protrusions 63 and 64 are formed in a triangular shape as shown in FIG. 22C. The stop tube 62 is formed in a shape similar to the stop tube 14 according to the second embodiment.

Now, an operation of the twelfth embodiment will be described here. After the clip unit 1 has been introduced, when the link member 51 is pulled toward the proximal end side, the end part 2c at the proximal end side of the clip 2 is pulled into the stop tube 62, and the clip 61 opens. At this time, as shown in FIG. 22B, the protrusions 63 and 64 of the clip 61 are engaged with each other, and the clip 61 is fixed in an opened state. When the link member 51 is further strongly pulled toward the proximal end side in this state, the protrusions 63 and 64 that are in engagement with each other slide along mutual inclined faces 63a and 64a, and are eventually disengaged each from the other. Further, the link member 51 is pulled toward the proximal end side, whereby the clip 61 can be closed.

According to advantageous effect of the present embodiment, at the protrusions 63 and 64 provided at the clip 61, the clip 61 is temporarily engagingly fixed in the maximum opened state. Thus, an operator can set the clip 61 to the maximum opened state merely by pulling the link member 51 to the proximal end side until the clip 61 has been engagingly fixed without worrying about the opened state of the clip 61, which simplifies manipulation.

In addition, the maximum opened state is stably maintained, and thus, a target tissue is easily captured, and tissue ligation can be carried out constantly.

Figure 23A:
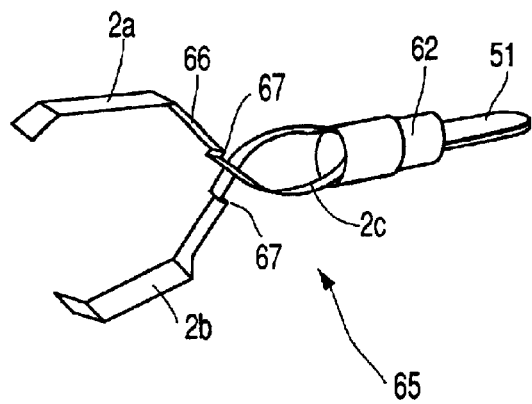
FIG. 23A and FIG. 23B each show a thirteenth embodiment according to the present invention, where
Figure 23B:
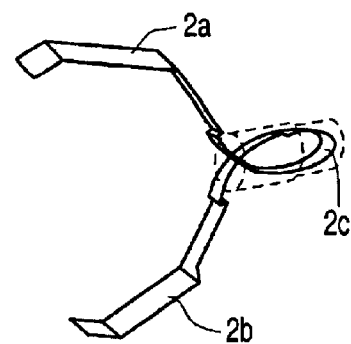

FIG. 23A and FIG. 23B each show a thirteenth embodiment according to the present invention. As shown in FIG. 23A, a clip unit 65 is composed of: a clip 66; the previously described stop tube 62; and the previously described link member 51.

The clip 66 is formed in a shape substantially similar to the clip 2 shown in the first embodiment. As shown in FIG. 23A, there are provided: arm sections 2a and 2b; a substantially circular proximal end part 2c; and a stepped section 67 of 0.5 mm to 1.5 mm in height between the arm sections 2a and 2b each and the proximal end part 2c.

Now, an operation according to the thirteenth embodiment will be described here. After the clip unit 65 has been introduced into a cavity, when the link member 51 is pulled against the proximal end side, the end part 2c at the proximal end side of the clip 65 is pulled into the stop tube 61, and the clip 2 is opened. At this time, as shown in FIG. 23B, a stepped section 67 of the clip 65 is engaged with the tip end side face of the stop tube 61, and the clip is fixed to be an opened state. When the link member 51 is further strongly pulled in this state, the stepped section 67 is deformed, and is disengaged from the stop tube 61, whereby the clip 2 can be closed. The advantageous effect according to the present embodiment is identical to that according to the twelfth embodiment. A duplicate description is omitted here.

Figure 24:
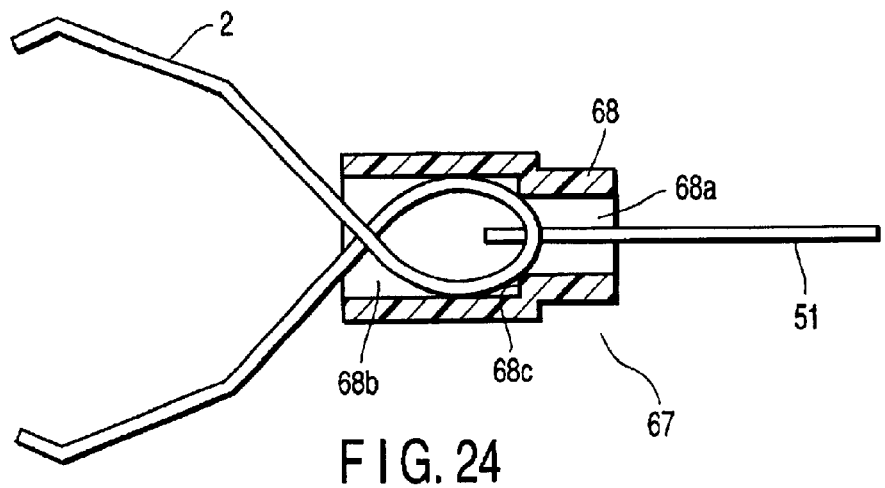
FIG. 24 shows a fourteenth embodiment according to the present embodiment, and is a longitudinal side view of a clip unit.

FIG. 24 shows a fourteenth embodiment according to the present invention. As shown in FIG. 24, the clip unit 67 is composed of: the previously described clip 2; a stop tube 68; and the previously described link member 51.

The stop tube 68 is formed in a substantially cylindrical shape, and the shape of the outer face is identical to that of the stop tube 14 according to the second embodiment. A large diameter section 68b smaller than an ellipse section dimension W of the clip 2 and a small diameter section 68a having a diameter smaller than the large diameter section 68b are provided on an internal cavity of the outer face, and a stepped section 68a is provided between the small diameter section 68a and the large diameter section 68b.

Now, an operation according to the fourteenth embodiment will be described here. After the clip unit 67 has been introduced into a cavity, when the link member 51 is pulled, a proximal end part 2c of the clip 2 is pulled into the stop tube 68, and the clip 2 opens. At this time, the end part 2c at the proximal end side of the clip 2 abuts against the stepped section 68c, and the clip is fixed in an opened state. When the link member 51 is further strongly pulled in this state, the end part 2c at the proximal end side of the clip 2 is pulled over the stepped section 68c of the stop tube 68 so that the clip 2 can be closed. The advantageous effect according to the present embodiment is identical to that according to the twelfth embodiment. A duplicate description is omitted here.

Figure 25:
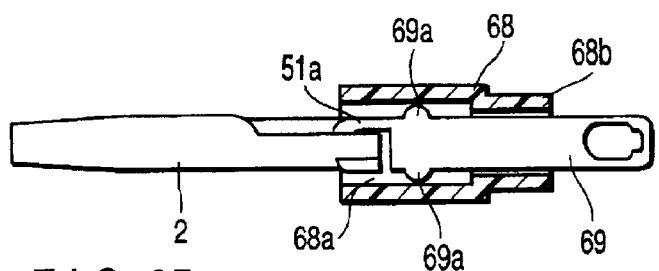
FIG. 25 shows a fifteenth embodiment according to the present invention, and is a longitudinal plan view of a clip unit.

FIG. 25 shows a fifteenth embodiment according to the present embodiment. A clipping apparatus according to the present embodiment, as shown in FIG. 25, is composed the previously described clip 2, the previously stop tube 68 and a link member 69.

The link member 69 is formed in the same shape as the link member 51 according to the ninth embodiment except that a circular or elliptical protrusion 69a is provided at the proximal end side of a claw shaped hook 51a. The protrusion 69a of the link member 69 is smaller than the large diameter section 68a of the previously described stop tube 68, and is slightly smaller than the diameter of the small diameter section 68b.

Therefore, when the link member 69 is pulled toward the proximal end side in order to open the clip unit 67, the protrusion 69a of the link member 69 abuts against the stepped section 68c of the stop tube 68, and the clip 2 is fixed in an opened state. When the link member 69 is further strongly pulled in this state, the protrusion 69a of the link member 69 is deformed, and is pulled into the small diameter section 68a of the stop tube 68, whereby the clip 2 is closed. The advantageous effect according to the present embodiment is identical to that according to the twelfth embodiment. A duplicate description is omitted here.

Figure 26:
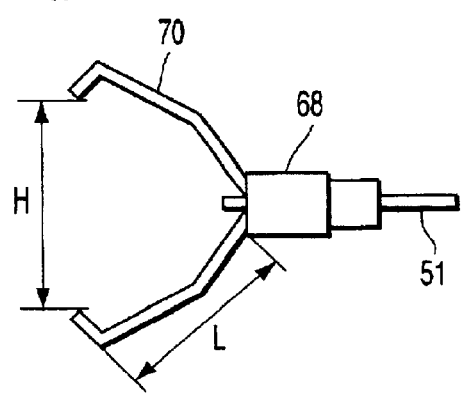
FIG. 26 shows a sixteenth embodiment according to the present invention, and is a side view of a clip unit.

FIG. 26 shows a sixteenth embodiment according to the present invention. A clipping apparatus according to the present embodiment is composed of a clip 70, the previously described stop tube 68, and the previously described line member 51 as shown in FIG. 26.

The clip 70 is molded by processing a thin plate of SEA alloy (Super Elastic Alloy) such as nickel titanium in a ribbon shape of 4 mm to 40 mm by press processing or the like, for example, and further, bending the center of the longitudinal direction of the ribbon in a V shape, as shown in FIG. 26. Therefore, a length L of an arm of the clip 70 ranges from 2 mm to 20 mm.

In addition, at this time, an opening width H of the clip 70, which is sufficient to ligate the tissue in a cavity, is bent in the range of 3 mm to 25 mm. A ribbon length (=clip arm length) varies depending on the opening width H of the clip 70. For example, when the opening width H is equal to 3 mm, the length L of the arm of the clip 70 is 2 mm (=ribbon length: 4 mm). When the opening length H is equal to 25 mm, the length L of the arm of the clip 70 is 15 mm.

Now, an operation according to the sixteenth embodiment will be described here. When the clip 70 is introduced into a cavity, the clip 70 is closed to 3 mm or less in outer diameter capable of being routed into the forceps channel of the endoscope, and is introduced. After the clip has been introduced, although the clip 70 is required to be opened to 3 mm to 25 mm in opening width sufficient to ligate tissues in a cavity, the clip 70 is made of SEA Alloy which is wide in an elastic area. Thus, the clip 70 closed in 3 mm in outer diameter capable of being routed into the forceps channel of the endoscope is sufficiently opened to be elastically restored to its original shape, and a tissue can be ligated.

When the endoscope is tightly curved, the arm sections of the clip 70, of a predetermined degree of hardness, is advanced with great difficulty along the forceps channel of the endoscope when the length L of the arm of the clip 70 exceeds 20 mm, thus increasing the insert resistance, of the clip into a cavity. On the other hand, when the length L of the arm of the clip 70 is shorter than 2 mm, the tissue at the deep part cannot be ligated. For example, in the case of hemostatis, the blood vessel at the deep part cannot be ligated, and thus, a sufficient hemostatic effect cannot be obtained. In addition, the blood vessel diameter of a bleeding site in bleeding in the peptic area often ranges from 1 mm to 3 mm in diameter. When the opening width H of the clip 70 is smaller than 3 mm, the blood vessels are ligated with difficulty. Conversely, when the opening width H exceeds 25 mm, an excessive amount of tissues is pinched between the arm sections of the clip 70, an amount of ligation force is reduced, and a sufficient hemostatic effect cannot be achieved.

Now, the advantageous effect according to the present embodiment will be described here. The clip 70 is made of a SEA alloy, and thus, can be elastically restored from a closed state capable of being inserted into the forceps channel of the endoscope to an opened state required to ligate the tissue in the cavity. Therefore, after the clip has been introduced into the cavity, there is no need to adjust the opening width of the clip during clip ligation, and operation is simplified. In addition, hemostatis of bleeding at the peptics must often be treated urgently. Thus, the clip is stored while it can be inserted into the forceps channel of the endoscope, and is ready to be used quickly in a case of emergency. In such a case, the clip 70 is stored to be closed to 3 mm or less in diameter over a long period of time.

However, the clip 70 according to the present embodiment is made of a SEA alloy, and thus, can be elastically and reliably restored to an opened state required to ligate the tissue in the cavity even after the closed state for a long period of time. Therefore, the desired opening width can always be obtained when the clip is used in an case of emergency. In addition, the clip is formed in a V shaped, and thus, both of the arms are disposed on a straight line, and can be reliably geared with each other without tip ends of the arm section being shifted during ligation.

Figure 27A:
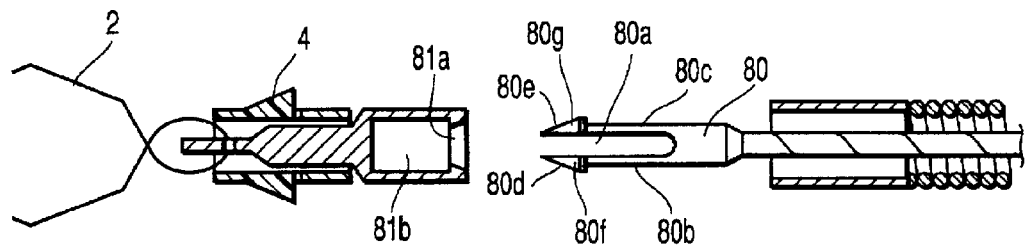
FIG. 27A to FIG. 27C each show a seventeenth embodiment according to the present invention, and is a longitudinally sectional side view of a clip unit and a clip manipulating device.
Figure 27B:
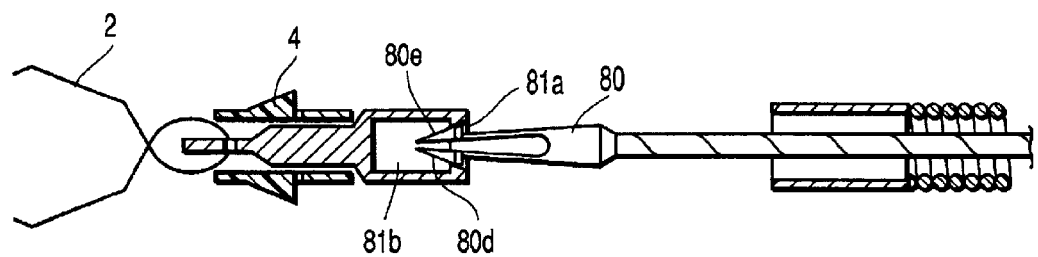
Figure 27C:
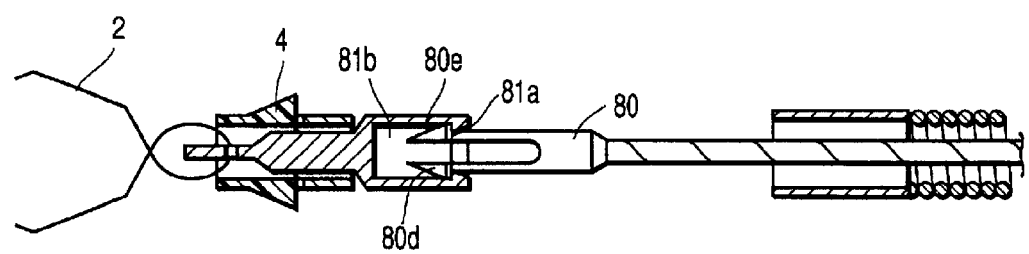
Figure 28A:
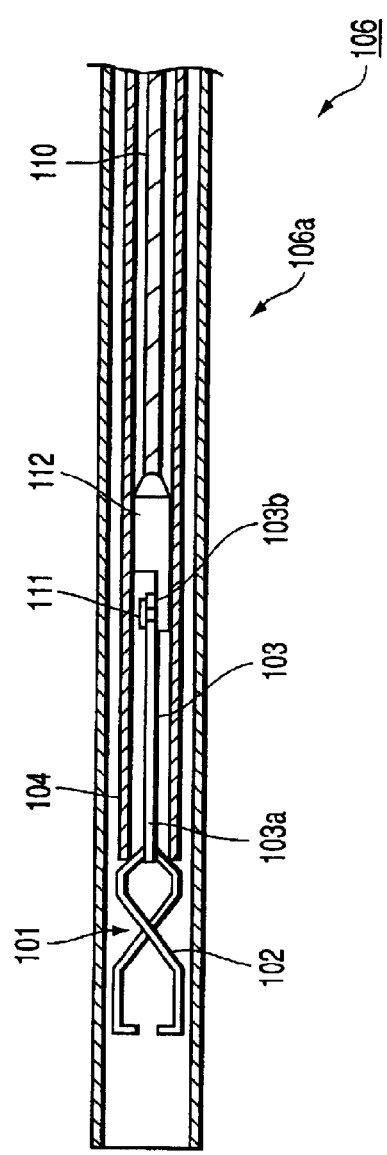
FIG. 28A and FIG. 28B each show a conventional example, where
Figure 28B:
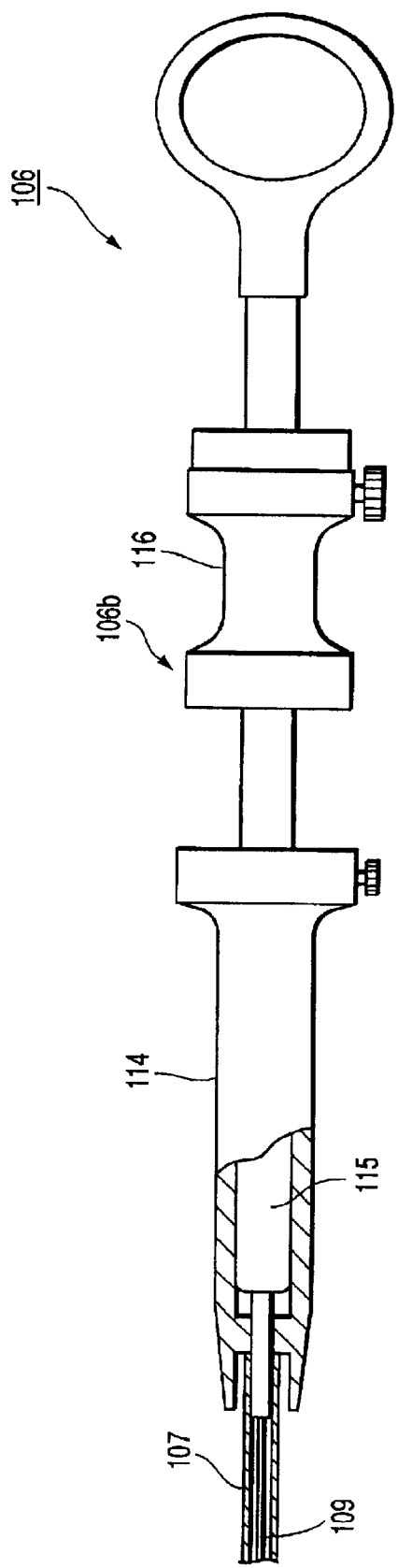

FIG. 27A to FIG. 27C each show a seventeenth embodiment according to the present invention. As shown in FIG. 27A to FIG. 27C, these figures each relates to a method of fixing the clip unit 1 and the clip manipulating device 5 to each other according to the first embodiment. The other configuration is the same as that according to the first embodiment except that the link member 3 of the clip unit 1 and the hook section 12 of the clip manipulating device 5 are different in shape.

According to the seventeenth embodiment, the hook section 80 is manufactured by molding/processing a resin having high strength such as a liquid crystal polymer or polyimide, for example. The hook section 80 is formed in a substantially cylindrical shape, and a slit 80a is provided at a tip end side as shown in FIG. 27A. Thus, arm sections 80b and 80c capable of being elastically deformed are formed at both sides of the slit 80a.

In addition, a structure is provided such that arrowhead hooks 80f and 80g each having an outer diameter than that of the arm sections 80b and 80c each are provided whose tip end is formed in a semi-cone shape having inclined faces 80d and 80e at the tip end side of the arm sections 80b and 80c, and the outer diameter of the arrowhead hooks 80f and 80g can be expanded/contracted due to elastic deformation of the arm sections 80b and 80c.

In addition, a link member 81 is formed in a hollow pipe shape at its proximal end side as shown in FIG. 27A. There are provided: a large diameter section 81b having an inner diameter greater than that of the arrowhead hooks 80f and 80g each of the previously described link member 80; and a small diameter section 81a having an inner diameter small than that of the previously described arrowhead hooks 80f and 80g each, and having an inner diameter greater than that of the arm sections 80b and 80c at the more proximal end side than the large diameter section. In addition, a claw hook 81c similar to that of the first embodiment is provided at a tip end side of the link member 81, and is hooked on the end part 2c at the proximal end side of the clip 2 so as to engage the clip 2.

Now, an operation according to the seventeenth embodiment will be described here. When the link member 81 is pushed at the tip end side of the hook section 80, the inclined faces 80d and 80e of the arrowhead hooks 80g and 80f of the hook section 80 abut against an internal face of the small diameter section 81a of the link member 81 as shown in FIG. 27B. When the link member is further pushed, the outer diameter of the arrowhead hooks 80g and 80f each is reduced along the inclined faces 80d and 80e. At this time, the arm sections 80b and 80c are elastically deformed. When the arrowheads 80g and 80f pass through the small diameter section 81a of the link section 81, as shown in FIG. 27C, the arm sections 80b and 80c are restored in the large diameter section 81b of the link member 81. Then, the arrowhead hooks 80g and 80f are engagingly fixed to a step between the small diameter section 81a and the large diameter section 81b. Otherwise, operation and advantageous effect according to the seventh embodiment are identical to those according to the first embodiment. A duplicate description is omitted here.

FIG. 29 to FIG. 34 each show an eighteenth embodiment according to the present invention. This embodiment relates to a clip unit and a clip manipulating device. A configuration according to the present invention is identical to that according to the first embodiment except that a clip unit 120 according to the present embodiment changes the link member 3 of the clip unit 1 according to the first embodiment, and adds a stop pipe 122.

In a clip manipulating device 130 according to the present embodiment, as shown in FIG. 33, the coil sheath 9 of the clip manipulating device 5 according to the first embodiment is composed of: a large diameter coil 135; a small diameter coil 136; and a connection portion 137. Further, a centering tube 131, an arrowhead hook 132, and a fixing chip 133 are added onto a manipulating wire 7.

The clip unit 120 is composed of a clip 2, a stop tube 4, a link member 121, and a stop pipe 122 as shown in FIG. 29. A hook section 121a engaged with the clip 2 is provided at a tip end side of the link member 121 as shown in FIG. 30 and FIG. 31.

Further, an elastic arm section 121b, an inclined face section 121d with an angle of 10 degrees to 90 degrees, and a small hole section 121c having an inner diameter greater than that of an axle section 132c of an arrowhead hook 132 described later are provided at the proximal end side of the link section 121. Therefore, the arrowhead hook 132 is pushed at the proximal end side of the link member 121, whereby the elastic arm section 121b is deformed and opened. When the hook is further pushed, the small hole section 121c can be engagingly fixed while the axle section 132c is pinched.

A fracture section 121e of 0.3 mm to 0.6 mm in outer diameter is provided at the link member 121. The link member 121 is pulled from a state of the clip unit 120 shown in FIG. 29 toward the proximal end side, whereby the clip 2 is closed. When the clip unit 120 is further pulled, the fracture section 121e breaks at about 2.5 kg to 4 kg.

In addition, a protrusion 121f that protrudes more greatly than the inner diameter of the stop tube 4 is provided at the link member 121, the protrusion 121f is pressed into the inner diameter of the stop tube 4 in a state of the clip unit 120, and thus, the stop tube 4 and the link member 121 are loosely fixed.

In addition, an axle section 121g is provided at the link member 121. As shown in FIG. 32, when the protrusion 4a provided at the stop tube 4 is protruded and recessed inside of the stop tube 4, a cylindrical shape of 0.6 mm to 1 mm in outer diameter is formed to prevent interference. A stop pipe 122 has an inner diameter greater than an outer diameter at the tip end side of the stop tube 4, and is provided so as to be engaged at the tip end side of the stop tube 4.

Figure 34:
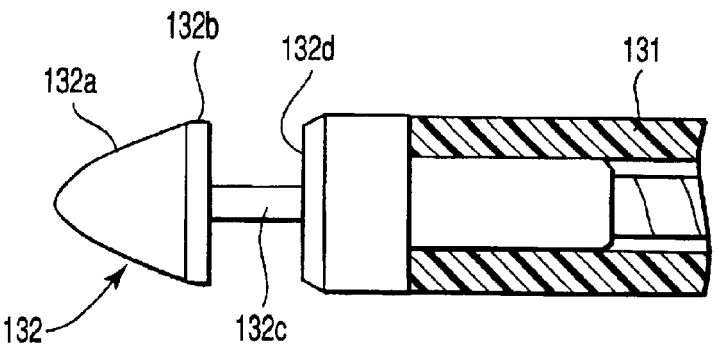
FIG. 34 is a side view showing an arrowhead hook according to the illustrative embodiment.

As shown in FIG. 33 and FIG. 34, the coil sheath 9 is composed of: a large diameter coil 135 having an inner diameter capable of housing the clip unit 122; a small diameter coil 136 having an inner diameter slightly greater than the outer diameter of the manipulating wire 7; and a connection portion 137 for connection the large diameter coil 135 and the small diameter coil 136. The connection portion 137 has an inner diameter that is greater than the outer diameter of the manipulating wire 7 and smaller than the outer diameter of a fixing chip.

A coil chip 8 is formed in a substantially tubular shape having an inner diameter identical to that of the coil sheath 9. In addition, the coil chip 8 is hard whereas the coil sheath 9 is flexible. In order to reduce a change of flexibility more significantly, a length of the coil chip 8 is about 0.5 to 3 times of an element line width of the coil sheath 9. In addition, the outer diameter at the tip end side of the coil chip 8 is contracted to be tapered in shape in consideration of endoscope insert properties. The coil chip 8 and the coil sheath 9 are connected to each other by laser welding in an abutted state without any special engagement structure.

In addition, the arrowhead hook 132 is fixed at a tip end of the manipulating wire 7, and is formed in a cone shape having the inclined face 132a at its tip end. The maximum outer diameter of the arrowhead hook 132 is defined as 1.0 mm to 1.4 mm in diameter in consideration of a deformation quantity of the elastic arm sections of the link member 121. In addition, it is desirable that the inclined face 132a is set to 30 degrees or less in order to smoothly ensure engagement with the link member 121.

The axle section 132c having an outer diameter smaller than the maximum outer diameter of the inclined face 132a is provided at the proximal end side of the inclined face 132a of the arrowhead hook 132, and a step is formed between the inclined face 132a and the axle section 132c so as to be reliably engaged with the elastic arm section 121b of the link member 121.

In addition, a vertical face 132d is provided at the further rear end side of the axle section 132c so that the force applied to the manipulating wire 7 when the clip unit 120 housed in the large diameter coil 135 is pushed forwardly of the large diameter coil 135 can be conveyed efficiently to the link member 121.

The centering tube 131 has an inner diameter greater than that of the manipulating wire 7 and an outer diameter smaller by about 0.05 mm to 0.3 mm than the inner diameter of each of the coil pipe 8 and the large diameter coil 135. This centering tube is provided so as to be covered over the manipulating wire 7 in the range of 0 mm to 300 mm at the tip end side of the manipulating wire 7, and is fixed by adhesive bonding or press-in to the fixing chip 133 provided on the arrowhead hook 132 and the manipulating wire 7.

The link member 121 is fabricated by ejection molding a resin having high strength such as a liquid crystal polymer or nylon and having proper elasticity. The stop pipe 122 is fabricated by processing a metal pipe made of stainless or the like.

The arrowhead hook 132 and the fixing chip 133 are fabricated by a metal such as stainless. The centering tube 131 is fabricated by a soft material such as Teflon or polyethylene.

According to the previously described eighteenth embodiment, as compared with the first embodiment, the link member 121 of the disposable clip unit 120 is made of a resin based elastic member, and a hook section of the clipping apparatus main body repeatedly used is made of a metallic non-elastic member, whereby, when the clip manipulating device 130 is repeatedly used, the device can be hardly broken.

In addition, the stop pipe 122 is engaged with the tip end side of the stop tube 4, whereby when the clip 2 is pulled into the stop tube 4, and a tissue is ligated, the stop tube 4 is prevented from being deformed or broken at its tip end part, thereby enabling reliable ligation.

According to the present embodiment, when the clip unit 120 is mounted on the arrowhead hook 132, the slider 11 is manipulated, and the manipulating wire 7 and the arrowhead hook 132 are protruded from the coil sheath 9. At this time, a gap between the inner diameter of the large diameter coil 135 and the outer diameter of the manipulating wire 7 is filled with the centering tube 131. Thus, even if the large diameter coil 135 is formed in any curved shape, the manipulating wire 7 is positioned at the axial center of the large diameter coil 135. Therefore, the arrowhead hook 132 protruded from the tip end of the large diameter coil 135 as well is positioned at the axial center of the large diameter coil 135.

Therefore, as shown in FIG. 14, when the clip unit 120 is sealed in a clip case 30, and the large diameter coil 135 and the clip unit 120 are positioned in axial direction, even when the large diameter coil 135 is formed in any shape, the arrowhead hook 132 is positioned at the axial center of the large diameter coil 135 merely by extruding the arrowhead hook 132 from the tip end of the large diameter coil 135, and thus, can be reliably engaged with the link member 121. In this way, in order to ensure that reliable alignment with the axial center is obtained whatever the large diameter coil 135 may be shaped, it is required to cover over the manipulating wire 7 the centering tube 121 at least by 20 mm or more or desirably by 50 mm or ore from a position very close to the arrowhead hook 132.

In addition, when the clip unit 120 housed in the large diameter coil 135 is extruded frontally of the large diameter coil 135, the manipulating wire 7 can push the clip unit 120 directly, without bending the inside of the large diameter coil 135. Thus, the clip unit 120 can be extruded efficiently with a smaller amount of force. Such positioning of the coil sheath 9 and the manipulating wire 7 or reduction of an amount of extrusion force provides similar advantageous effect in all the treatment utensils for protruding a treatment section from the inside of the sheath such as snare, basket, injection needle, or retainer snare as well as the clip manipulating device.

In addition, an inner diameter of the connection portion 137 is smaller than an outer diameter of the fixing chip 133. Thus, when the manipulating wire 7 is pulled, the wire interferes with the connection portion 137, whereby the manipulating wire 7 can be prevented from being pulled into the coil sheath 134 than necessary. In addition, the coil ship 9 is structured to be welded and fixed merely by butting, instead of an engagement structure, making it possible to reduce a hard section in size, and facilitate insertion into the endoscope.

In addition, processing of the coil chip 8 and coil sheath 8 is simplified, and the chip and sheath can be manufactured inexpensively.

Figure 35:
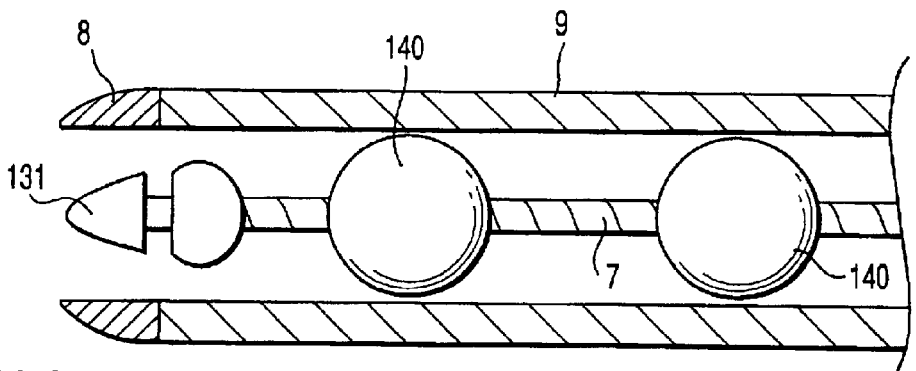
FIG. 35 shows a nineteenth embodiment according to the present embodiment, and is a longitudinally sectional side view of a coil sheath.

FIG. 35 shows a nineteenth embodiment according to the present invention. A clip manipulating device according to the present invention is identical to that in any other configuration except that the centering tube 131 according to the eighteenth embodiment is merely changed.

That is, as shown in FIG. 35, instead of the centering tube 131 shown in the eighteenth embodiment, a total of two centering chips 140 are provided at a position of 0 mm to 10 mm and at a position of 20 mm to 50 mm each from the end part at the proximal end of the arrowhead hook 132. In this way, a plurality of centering chips 140 are provided over a predetermined range, thereby making it possible to stably position the manipulating wire 7.

The centering chip 140 is fabricated from a hard material such as a metal, for example, and is formed in a substantially spherical shape having an outer diameter greater than that of the manipulating wire 7 and smaller than the inner diameter of the large diameter coil 135.

The centering chip 140 may be molded by injection molding a hard resin such as a liquid crystal polymer or nylon, or alternatively, a soft resin such as silicon or Teflon onto the manipulating wire 7.

The operations and advantageous effects according to the present embodiment are similar to those according to the eighteenth embodiment.

Figure 36:
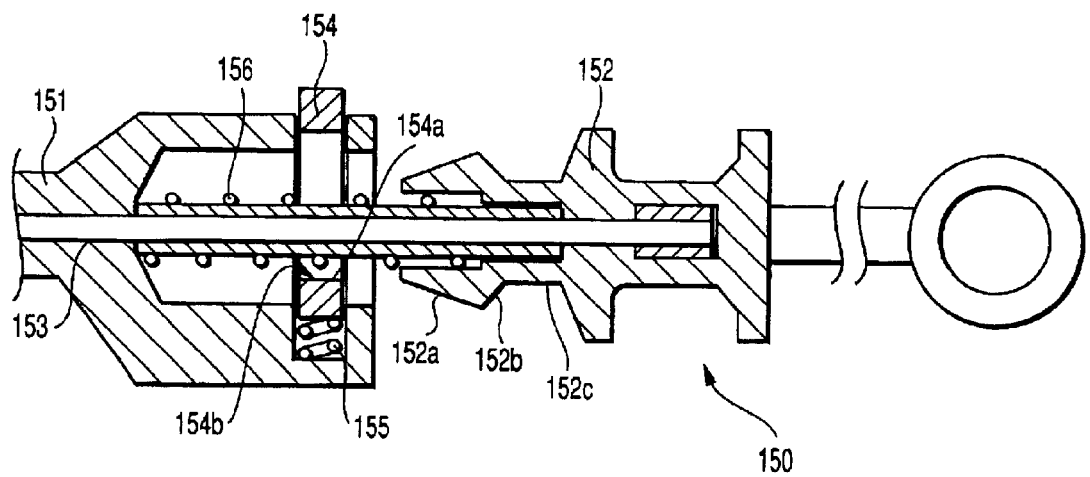
FIG. 36 shows a twentieth embodiment according to the present embodiment, and is a longitudinally sectional side view showing a manipulating section of a clipping apparatus.
Figure 37:
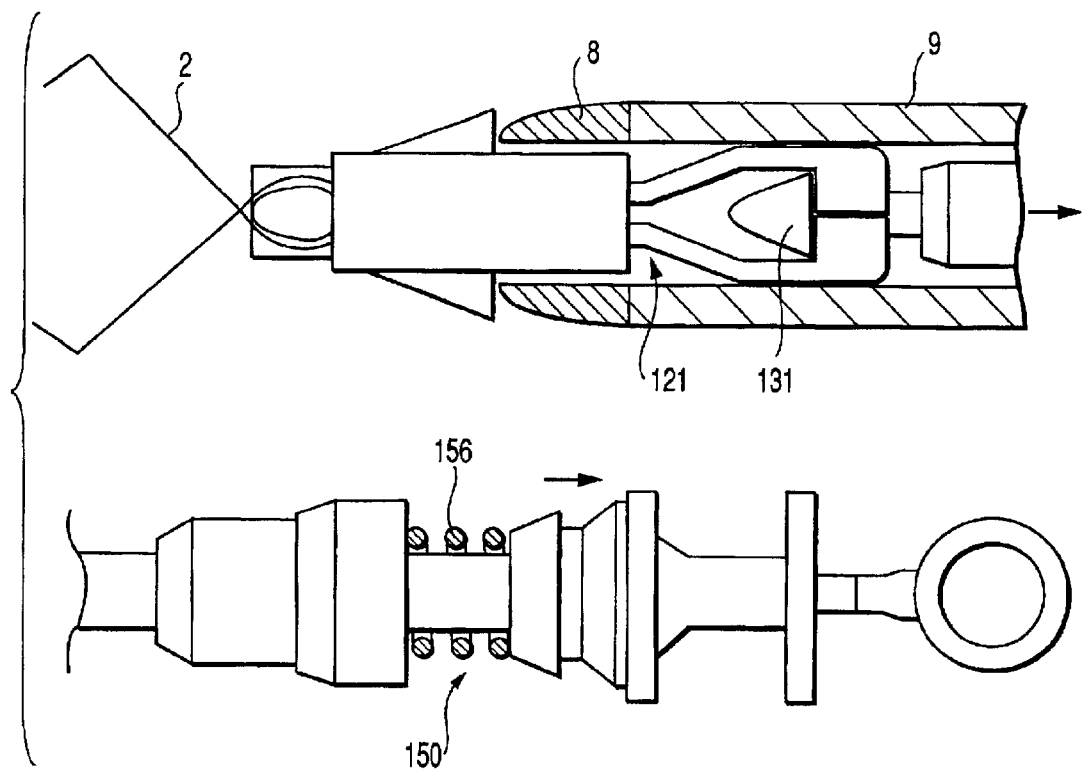
FIG. 37 shows the illustrative embodiment, and is a sectional side view of a part of the clipping apparatus.

FIG. 36 and FIG. 37 each show a twentieth embodiment according to the present invention. This embodiment relates to a manipulating section 150 of the clip manipulating device 130 according to the eighteenth embodiment.

The manipulating section 150 is composed of a manipulating section main body 151, a slider 152, a manipulating pipe 153, a lock 154, a lock spring 155, and a slider spring 156. The coil sheath 9 is mounted at the tip end side of the manipulating section main body 151. The slider 152 is slidably provided in the horizontal direction in the figure at the manipulating section main body 151. The manipulating pipe 153 is mounted on the slider 152, and further, the manipulating wire 7 is mounted on the manipulating pipe 153. The lock 154 is slidably provided in the vertical direction in the figure at the manipulating section main body 151, and is always biased upwards in the figure by the lock spring 155.

An inclined face 152a having an acute angle (from about 10 degrees to 90 degrees) and an inclined face 152b having an obtuse angle (greater than an angle of the inclined face 152a) are provided at the tip end side of the slider 152. An inner diameter of the lock 154 is greater than an outer diameter of the inclined face 152a of the slider 152.

Now, an operation according to the twentieth embodiment will be described here.

When the slider 152 is slid to the tip end side, the inclined face 152a of the slider 152 abuts against the proximal side end face 154a of the inner diameter of the lock 154. If the slider 152 is further slid to the tip end side in this state, the lock 154 is pushed down by the inclined face 152a of the slider 152. At this time, the inclined face 152a is an acutely angled inclined face, and thus, the lock 154 can be pushed down with a small amount of force.

When the slider 152 is further slid to the tip end side, the inclined face 152a of the slider 152 moves to the tip end side over the lock 154. Then, the lock 154 abuts against a small diameter section 152c of the slider 152 by the lock sprint 155. At this time, although the slider 152 is pushed against the proximal end side at the slider spring 156, the inclined face 152b is obtusely angled. Thus, an amount of push force of the slider spring 156 is smaller than that of the lock 154 rolling over the tip end side end face 154b, and the slider 152 is temporarily fixed.

When the slider 152 is strongly pulled toward the proximal end side in this state, the lock 154 is pushed down by the inclined face 152b, and the slider 152 slips out of the lock 154, thus making it possible to release the slider 152 from a fixed state.

According to the present embodiment, two inclined faces 152a and 152b with different angles are provided at the tip end side of the slider 152, whereby an amount of force of vertically sliding the lock 154 can be changed. The slider 152 is pushed against the tip end side, whereby the slider 152 can be fixed with a gentle push, and can be released by pulling it strongly. Therefore, the slider 152 itself can be fixed/released merely by manipulation of the slider 152 without providing a mechanism such as specially fixed ON/OFF button, and the clip unit 120 can be mounted/removed easily and speedily.

In addition, a slider spring 156 for biasing the slider 152 at the proximal end side is provided, whereby the clip unit 120 is engaged with a tip end of the coil sheath 9, as shown in FIG. 37, and the clip unit 120 can be automatically engaged with the coil sheath 9 while the clip unit is approached to a target physiological tissue, and stable manipulation can be carried out.

Figure 38:
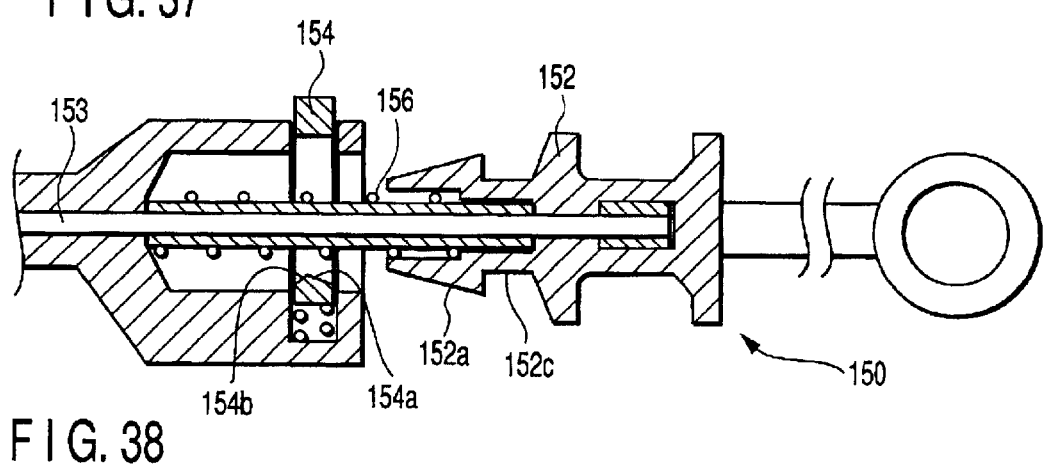
FIG. 38 shows a first modified example according to the illustrative embodiment, and is a longitudinally sectional side view showing a manipulating section of a clipping apparatus.
Figure 39:
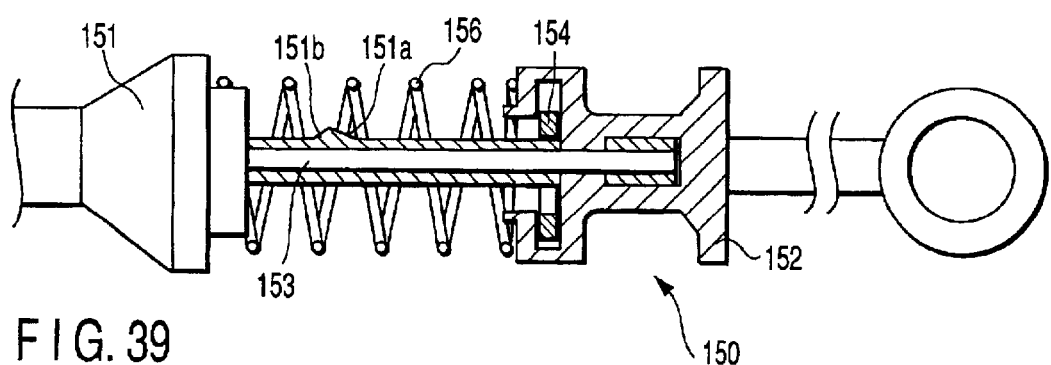
FIG. 39 shows a second modified example according to the illustrative embodiment, and is a longitudinally sectional side view showing a manipulating section of a clipping apparatus.
Figure 47:
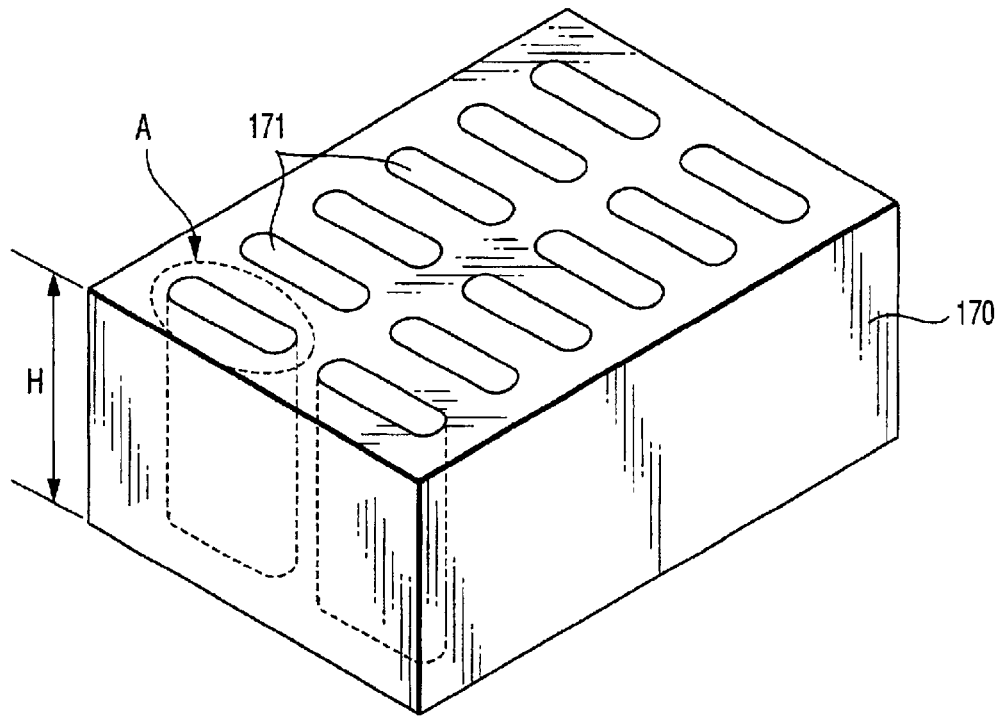
FIG. 47 shows a twenty fifth embodiment according to the present invention, and is a perspective view of a frame for sealing a clip case.
Figure 48:
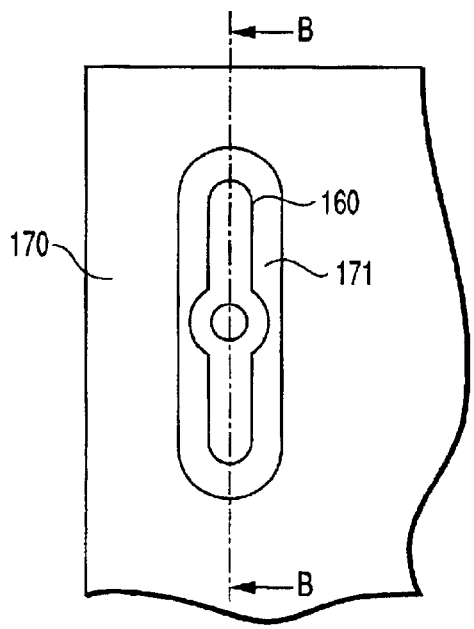
FIG. 48 shows the illustrative embodiment, and is an enlarged plan view of a section A shown in FIG. 47.

According to a first modified example of the present invention, as shown in FIG. 38, two inclined faces 154a and 154b with different angles may be provided at the lock 154. Further, according to a second modified example, as shown in FIG. 39, the lock 154 may be provided on the slider 152, and two inclined faces 151a and 151b with different angles may be provided at the manipulating section main body 151.

In addition, a slider fixing mechanism according to the present embodiment provides similar advantageous effect in all the treatment utensils for protruding a treatment section from the inside of the sheath such as snare, basket, injection needle, and retainer snare as well as clip manipulating device.

FIG. 40 to FIG. 43 each show a twenty first embodiment according to the present invention. The present embodiment relates to a clip case 160 for sealing the clip unit 120 according to the eighteenth embodiment. That is, the clip case 160 is composed of two parts, a case main body 161 and a case cover 162 as shown in FIG. 40. The case main body 161 and the case cover 162 are manufactured by ejection molding a properly hard and transparent resin such as ABS or polystyrene, for example. As shown in FIG. 41, a total of six engagement claws 161a are provided on the internal face of the case main body 161. These claws are engaged with engagement holes 162a provided at the case cover 162 over a total of six parts that correspond to the engagement claws 161a, whereby the claws are assembled in the state shown in FIG. 40. Therefore, the clip unit 120 is assembled after being disposed between the case main body 161 and the case cover 162, whereby the clip unit 120 can be sealed into the clip case 160.

At the case main body 161 and the case cover 162, semi-circular grooves 161b and 162b are provided in a right side half on the paper face, and are diverged in a tapered shape on the end face. Therefore, in an assembly state as shown in FIG. 40, a circular hole 163 is formed by a semi-circular groove 161b of the case main body 161 and a semi-circular groove 162b of the case cover 162, as shown in FIG. 42. The circular hole 163 has an inner diameter greater than an outer diameter of the coil sheath 9 of the previously described clip manipulating device 130. In addition, on the end face, there is formed a funnel section 163a diverged in a funnel shape up to a diameter that is 1.5 times to 3 times as large as the inner diameter of the circular hole 163.

At the center of the case main body 161 and the case cover 162, as shown in FIG. 43A and FIG. 43B, a small diameter section 164 smaller than an inner diameter of the coil pipe 9 and greater than an outer diameter of the stop tube 4 are provided at the upper left side on the paper face of the previously described circular hole 163. An inclined face section 165 is provided at the further left side of the small diameter section 164, and communicates with a link member storage section 166. An elastic arm section of the link member 121 is formed at the link member storage section 166 in sufficient width free of interference even when the arm section is deformed by insertion of the arrowhead hook.

A stop tube storage section 167 having an inner diameter slightly greater than the outer diameter of the stop tube 4 is provided at the further left side of the link member storage section 166. A clip storage section 168 for storing the clip 2 is provided at the further left side of the stop tube storage section 167.

In addition, coil fixing arms 169 and 170 are provided in the vicinity of the small diameter section 164 on the circular hole 163. As shown in FIG. 42, the coil fixing arm is composed of: coil fixing sections 169a and 170a that are protruded by about 0.1 mm to 0.5 mm in the inner diameter direction of the circular hole 163; and arm sections 169b and 170b that are protruded by about 0.5 mm to 3 mm.

Now, an operation according to the twenty first embodiment will be described here.

First, the slider 152 of the clip manipulating device 150 according to the eighteenth to twentieth embodiments is pushed out toward the tip end side, and the arrowhead hook 131 is protruded from the tip end of the coil sheath 9. At this time, the slider 152 is fixed by the lock 154. In this state, a tip end of the coil sheath 9 is inserted into the circular hole 163 through the funnel section 163a of the clip case 160. When the coil sheath 9 reaches the coil fixing arms 169 and 170, the arm sections 169b and 170b are deformed by the pushing force of the coil sheath 9, and the coil fixing sections 169a and 179a broaden.

In this state, the coil sheath 9 is pushed until the end part at the tip end side of the coil sheath 9 abuts against a step between the circular hole 163 and the small diameter section 164. At this time, the arm sections 169b and 170b are elastically deformed, and the coil sheath 9 is sandwiched between the coil fixing sections 169a and 170a. Thus, the coil sheath 9 is loosely fixed to the clip case 160.

When the coil sheath 9 is pushed until the sheath has abutted against the inside of the clip case 160, the arrowhead hook 131 is protruded from the tip end of the coil sheath 8. Thus, the arrowhead hook 131 passes through the small diameter section 164 of the clip case 160, and is pushed into the link member storage section 166. At this time, the circular hole 163 and the stop tube storage section 167 are aligned at the axial center. Thus, the arrowhead hook 131 is reliably pushed against the proximal end side of the link member 121 disposed in the link member storage section 166, and the link member 21 and the arrowhead hook 131 are engaged with each other.

At this time, the inclined face section 121d is provided at the link member 121. Thus, even when the arrowhead hook 131 is displaced slightly vertically, the hook abuts against the inclined face section 121d, and is reliably engaged after the displacement has been corrected in the center direction.

In addition, the clip case 160 is manufactured by a transparent material. Thus, the presence or absence of the clip unit 120 in the clip case 160 or a state of engagement between the link member 121 and the arrowhead hook 131 can be visually checked.

After checking the link member 121 and the arrowhead hook 131 for engagement, if the slider 152 is pulled toward the proximal end side, the manipulating wire 7 is pulled, and the arrowhead hook 131 and the clip unit 120 are pulled into the coil sheath 9. At this time, the protrusion 4a of the stop tube 4 abuts against the inclined face section 165 of the case main body 161 and the case cover 162. The protrusion 4a is pushed into the direction inside of the stop tube 4, and can be pulled into the coil sheath 9 without being engaged with an end face of the coil pipe 8. Then, the coil sheath 9 is strongly pulled, and is pulled out of the clip case 160.

According to the present invention, the clip unit 160 can be easily assembled by merely pushing the clip case main body 161 into the case cover 162, and manufacturing cost can be reduced. In addition, the coil fixing arms 169 and 170 are provided, whereby the clip case 160 and the coil sheath 9 can be fixed to each other. In addition, the clip unit 120 can be easily mounted without the need to have both of the coil sheath 9 and the clip case 160. Further, the clip unit 120 is composed of a transparent material, thereby making it possible to check the clip unit 120 in the clip case 160 for presence or absence or check the link member 121 and the arrowhead hook 131 for engagement. In this manner, the clip unit 120 can be reliably mounted.

FIG. 44 shows a twenty second embodiment according to the present invention. According to the present embodiment, coil fixing protrusions 180 and 181 are provided at the inner diameter side of the circular hole 163 by eliminating the coil fixing arms 169 and 170 according to the twenty first embodiment. The coil sheath 9 is fixed by elastic deformation of the case main body 161 and the case cover 162 themselves, instead of deformation of the arm sections 169b and 170b.

According to the present embodiment, there is no need to provide an arm section, and an ejection molding die can be easily fabricated. The other advantageous effects are the same as those of the twenty first embodiment.

FIG. 45 shows a twenty third embodiment according to the present invention. According to the present embodiment, arm sections 169b and 170b are provided at an angle protruded in the inner diameter direction of the circular hole 163 by eliminating the coil fixing sections 169a and 170a of the coil fixing arms 169 and 170 according to the twenty first embodiment. The arm sections 169b and 170b are deformed in direct abutment against the coil sheath 9, thereby fixing the coil sheath 9. The advantageous effect of the present embodiment is the same as that of the twenty first embodiment.

FIG. 46 shows a twenty fourth embodiment according to the present invention. According to the present embodiment, a soft resin based O ring 182 such as silicon is provided at the inner diameter side of the circular hole 163 by eliminating the coil fixing arms 169 and 170 according to the twenty first embodiment. The coil sheath 9 is fixed by elastic deformation of the O ring 182 instead of deformation of the arm section.

According to advantageous effect of the present invention, there is no need to provide a protrusion, and an ejection molding die can be easily fabricated. In addition, the coil sheath 8 is fixed at its entire periphery by the O ring 182, and thus, an amount of fixing force is stabilized.

FIG. 47 to FIG. 51 each show a twenty fifth embodiment according to the present invention. The present invention relates to a frame 170 for arranging and sealing a plurality of clip cases shown in the twenty first to twenty fourth embodiments.

Figure 49:
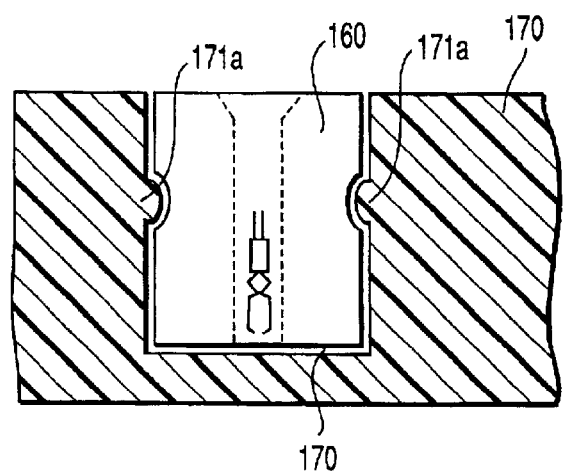
FIG. 49 shows the illustrative embodiment, and is a cross section taken along the line B—B shown in FIG. 48.

At the frame 170, a total of 12 case insert holes 171 are provided while one side into which the clip case 160 can be inserted is closed. It is desirable that 3 to 24 case insert holes 171 be provided in consideration of the size of the entire frame 170. In addition, a height H of the frame 170 is defined to be greater than the height of the clip case 160. At the case insert hole 171 of the clip case 160, as shown in FIG. 49, a fixing protrusion 171a for fixing the clip case 160 is provided to be pressed-in and fixed by inserting the clip case 160. The clip case 160 can be fixed more securely by providing an engagement groove at a position that corresponds to the fixing protrusion 171a of the frame 170 on the clip case 160.

Figure 50:
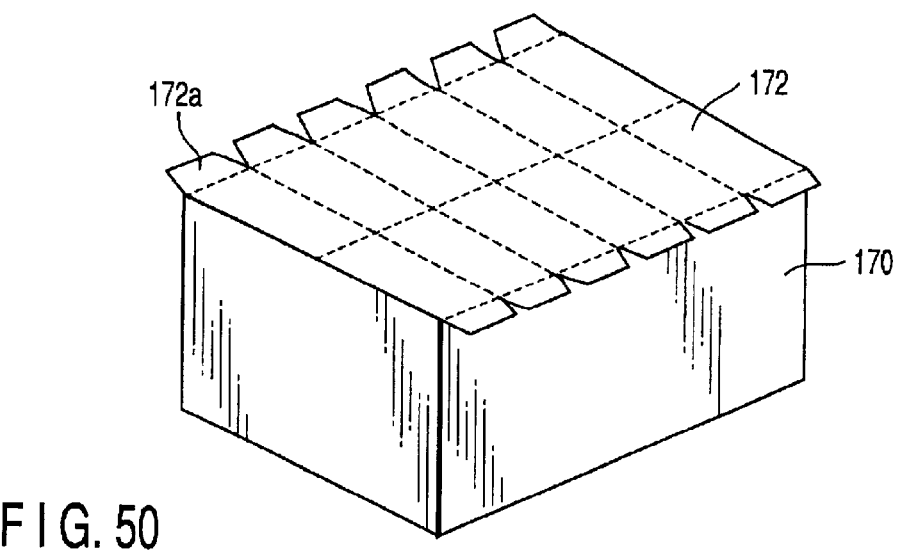
FIG. 50 is a perspective view of a frame for sealing a clip case according to the illustrative embodiment.
Figure 51:
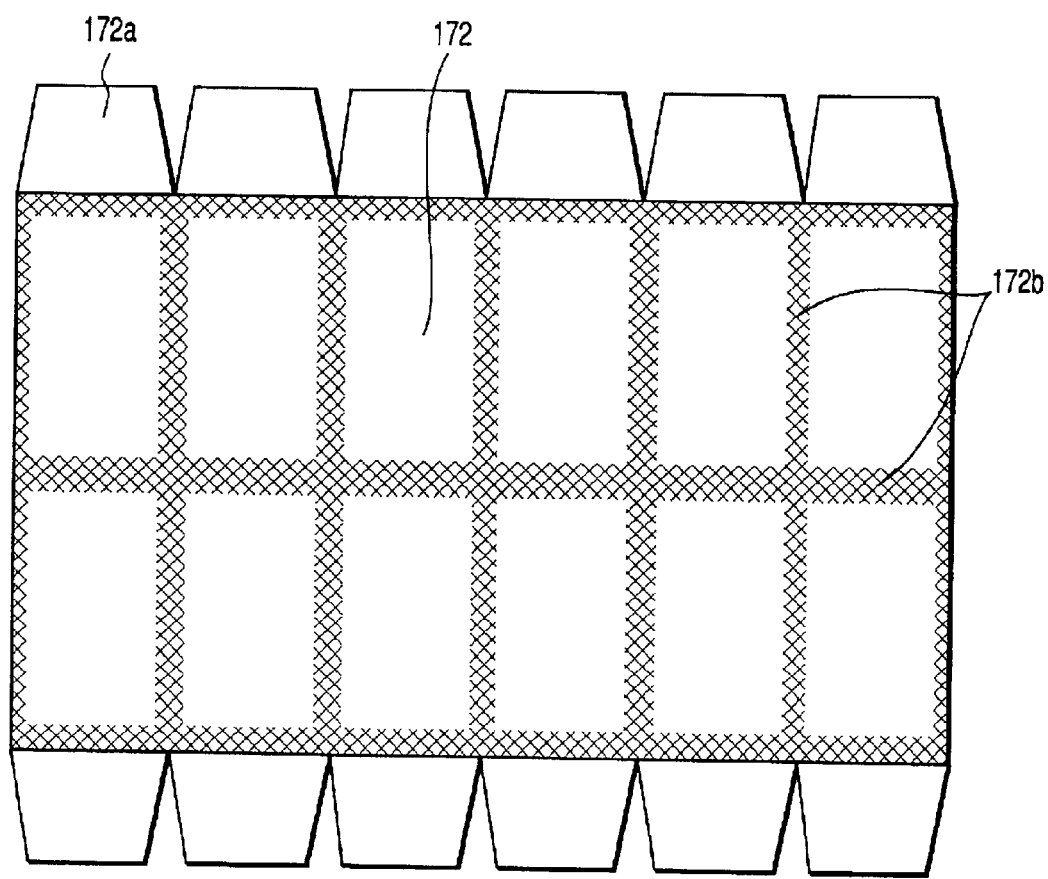
FIG. 51 shows the illustrative embodiment, is a plan view of a frame for sealing a clip case.

The clip case 160 having the clip unit 120 sealed therein is pushed into the case insert hole 171 of the frame 170 while the funnel section 164 of the clip case 160 is oriented to the opening side of the case insert hole 171. After the click case 160 has been pushed into all the case insert holes 171, as shown in FIG. 50 and FIG. 51, the sealing paper 171 is heat-sealed so as to close the case insert hole 171.

This sealing paper 172 is heat-sealed in a panel shape so as to seal a respective one of the case insert holes 171 independently. The sealing paper 172 is made of a material that passes sterilization gas (ethylene oxide gas), and perforation is provided on the sealing paper 172 along the panel shaped sealing section 172b so as to open the case insert holes 171 one by one. In addition, a peeling section 172a is provided while a part of the sealing paper 172 is extruded from the frame 170. In this state, sterilization is carried out by ethylene oxide gas or the like. The frame 170 is fabricated by blow molding polypropylene or ejection molding ABS or polystylene.

The above described peeling section 172a is peeled by hand in order to mount the clip unit 120 on the clip manipulating device 5. At this time, the sealing paper 172 is peeled while the paper is cut along the perforation. Thus, only the case insert hole 171 having the desired clip unit 120 sealed therein can be opened. Then, the clip unit 120 can be mounted on the clip manipulating device 5 in the same way as the twenty first embodiment.

According to the present embodiment, the clip case 120 is sealed in the frame 170, whereby the frame 170 can be stably placed on a work board such as desk, for example. The clip manipulating device 5 is merely gripped and manipulated without taking the clip case 120, whereby the clip unit 120 can be mounted on the clip manipulating device 5. In addition, the peeling section 172a and perforation are provided at the sealing paper 172, whereby the sealing paper 172 can be peeled reliably one by one corresponding to the case insert holes 171, and manipulation is simplified.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A physiological tissue clipping apparatus comprising:
   an clip capable of being arbitrarily opened/closed;
   a tightening ring engagingly mounted on the clip, thereby closing the clip;
   a link member capable of being inserted into the tightening ring and engaged with the clip;
   an introducing tube capable of housing the clip and the tightening ring;

a manipulating member retractably routed into the introducing tube; and engagement means provided at least one of the tightening ring and the introducing tube, the engagement means engaging the introducing tube with the tightening ring when the clip and tightening ring protrudes in front of the introducing tube, and disabling the tightening ring from being housed again in the introducing tube.

2. An apparatus according to claim 1, wherein said engagement means is provided at said tightening ring.

3. An apparatus according to claim 2, wherein said engagement means is a protrusion that is protruded in a radial direction of the tightening ring when said tightening ring is protruded frontally of the introducing tube, and is engaged with said introducing tube.

4. An apparatus according to claim 1, wherein said engagement means is provided at said introducing tube.

5. An apparatus according to claim 1, wherein said introducing tube comprises a member having flexibility capable of being introduced into a body cavity via a soft endoscope.

6. An apparatus according to claim 1, wherein said manipulating member comprises a wire having flexibility capable of being introduced into a body cavity via a soft endoscope.

7. An apparatus according to claim 1, comprising a clip cover for sealing the clip, the tightening ring, and the link member while said link member is further engaged with said clip and said tightening ring is engagingly mounted on said link member, said clip cover further enabling housing the tightening ring in the introducing tube.

8. An apparatus according to claim 7, wherein said clip cover comprises a diameter reducing means for reducing said engagement means to a diameter capable of being housed in said introducing tube.

9. A physiological tissue clipping apparatus comprising:

a clip capable of being arbitrarily opened/closed;

a tightening ring engagingly mounted on the clip, thereby closing the clip;

a link member capable of being inserted into the tightening ring and engaged with the clip;

an introducing tube capable of mounting the clip and the tightening ring at a distal end thereof;

a manipulating member retractably routed into the introducing tube; and a cover provided on the clip capable of entering an opened state required to ligate a physiological tissue from a closed state capable of being inserted into an endoscope.

10. An apparatus according to claim 9, wherein said cover is refracted to a proximal end side, whereby said clip is released from the cover, and is established in an opened state.

11. An apparatus according to claim 9, wherein said cover advances to its distal end side, and slips out of said clip, whereby said clip is released from the cover, and is established in an opened state.

12. An apparatus according to claim 9, wherein said cover is broken, whereby said clip is released from the cover, and is established in an opened state.

13. An apparatus according to claim 9, wherein said cover is opened, whereby said clip is released from the cover, and is established in an opened state.

14. An apparatus according to claim 9, wherein said cover is dissolved, whereby said clip is released from the cover, and is established in an opened state.

15. An apparatus according to claim 9, wherein said introducing tube comprises a member having flexibility capable of being introduced into a body cavity via a soft endoscope.

16. An apparatus according to claim 9, wherein said manipulating member comprises a wire having flexibility capable of being introduced into a body cavity via a soft endoscope.

17. A physiological tissue clipping apparatus comprising a clip unit including:

a clip capable of being arbitrarily opened/closed;

a tightening ring engagingly mounted on the clip, thereby closing the clip, and;

a link member capable of being inserted into the tightening ring and engaged with the clip, thereby transferring a force that retracts the clip into the tightening ring to the clip; and a clip manipulation device which is a separate body from the clip unit including:

a hook capable of being engaged with the link member of the clip unit and a manipulating wire transferring the force that retracts the clip into the tightening ring to the hook, wherein at least one of the link member and the hook is elastically deformable, the link member and the hook define an engagement structure wherein based on deformation and restoration of shape of one of the link member and the hook, the one of the link member and the hook is engaged with the other one of the link member and the hook and the clip unit is engaged with the clip manipulation device by the engagement structure.

18. An apparatus according to claim 17, wherein said deformation means is provided at said hook.

19. An apparatus according to claim 17, wherein said deformation means is provided at said link member.

20. An apparatus according to claim 17, wherein said deformation means are provided at said link member and the hook.

21. An apparatus according to claim 17, wherein an arm section having closing properties and a pinch section for pinching and fixing a proximal end part of said link member are provided at said hook.

22. An apparatus according to claim 17, wherein an arm section having closing properties and a pinch section for pinching and fixing a distal end part of said hook are provided at said link member.

23. An apparatus according to claim 17, wherein an internal cavity whose distal end side is small in diameter is provided at said hook, and a proximal end part whose outer diameter can be expanded/reduced is provided at said link member so that said hook and the link member can be engagingly fixed to each other.

24. An apparatus according to claim 17, wherein an internal cavity whose tip end side is small in diameter is provided at said link member, and a tip end part whose outer diameter can be expanded/reduced is provided at said hook so that said hook and the link member can be engagingly fixed to each other.

25. An apparatus according to claim 17, wherein said deformation means is an elastic member.

26. An apparatus according to claim 17, comprising a clip cover for sealing the clip, the tightening ring, and the link member while said link member is further engaged with said clip and said tightening ring is engagingly mounted on said link member, said clip cover further enabling engagement between said link member and said hook.

27. An apparatus according to claim 17, wherein said link member is a resin-based elastic member, and the hook provided at said manipulating member distal end is a metallic non-elastic member.

28. A physiological tissue clipping apparatus comprising:
a clip capable of being arbitrarily opened/closed;
a tightening ring engagingly mounted on the clip, thereby closing the clip;
a link member engaged with the clip, thereby transferring a force that retracts the clip into the tightening ring to the clip; and
holding means for, stopping the clip from being further retracted into the tightening ring when the clip is opened to the maximum, thereby temporarily maintaining the opened state,
wherein the holding means has a holding force that permits release of the clip from the opened state when the clip is pulled, after the opened state is maintained, with a force greater than the force used to retract the clip until the clip is opened to the maximum.

29. An apparatus according to claim 28, wherein said holding means is provided at said clip.

30. An apparatus according to claim 28, wherein said holding means is provided at said tightening ring.

31. An apparatus according to claim 28, wherein said holding means is provided at said link member.

32. An apparatus according to claim 28, wherein said clip comprises arms and said holding means is a stepped section that is provided at each of the arms of said clip, for engaging said arms to each other.

33. An apparatus according to claim 28, wherein said clip comprises arms and said holding means is a stepped section that is provided at each of the arms of said clip, for engaging said arms with said tightening ring.

* * * * *